(12) United States Patent
Herron et al.

(10) Patent No.: US 9,586,059 B2
(45) Date of Patent: Mar. 7, 2017

(54) USER INTERFACE FOR GUIDED RADIATION THERAPY

(75) Inventors: Matthew A. Herron, Palo Alto, CA (US); Brian W. Epps, Seattle, WA (US); Kevin G. Rolfes, Redmond, WA (US); David P. Swanson, Kirkland, WA (US); Luis R. Retana, San Diego, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1860 days.

(21) Appl. No.: 11/189,542

(22) Filed: Jul. 25, 2005

(65) Prior Publication Data
US 2006/0063999 A1 Mar. 23, 2006

Related U.S. Application Data

(60) Provisional application No. 60/590,699, filed on Jul. 23, 2004.

(51) Int. Cl.
*A61B 5/05* (2006.01)
*A61N 5/10* (2006.01)

(52) U.S. Cl.
CPC .... *A61N 5/1049* (2013.01); *A61N 2005/1074* (2013.01)

(58) Field of Classification Search
None
See application file for complete search history.

(56) References Cited

U.S. PATENT DOCUMENTS

| | | |
|---|---|---|
| 3,967,161 A | 6/1976 | Lichtblau |
| 4,023,167 A | 5/1977 | Wahlstrom |
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson et al. |
| 4,260,990 A | 4/1981 | Lichtblau |
| 4,393,872 A | 7/1983 | Reznik et al. |
| 4,618,822 A | 10/1986 | Hansen |
| 4,633,250 A | 12/1986 | Anderson |

(Continued)

FOREIGN PATENT DOCUMENTS

| | | |
|---|---|---|
| DE | 19914455 A1 | 10/2000 |
| EP | 0531081 A1 | 1/1992 |

(Continued)

OTHER PUBLICATIONS

U.S. Appl. No. 60/590,503, filed Jul. 23, 2004, Wright et al.

(Continued)

*Primary Examiner* — Joel F Brutus
(74) *Attorney, Agent, or Firm* — Perkins Coie LLP

(57) ABSTRACT

A facility for presenting a visual user interface for guiding the performance of a process relating to a patient localization and tracking system is described. The facility displays the user interface in a first state that corresponds to a first process task in an ordered sequence of process tasks. Each time the process task to which the displayed state of the user interface corresponds is completed, the facility redisplays the user interface in a state corresponding to a process task following the process task to which the displayed state of the user interface corresponds.

22 Claims, 28 Drawing Sheets

(56) References Cited

U.S. PATENT DOCUMENTS

| | | | |
|---|---|---|---|
| 4,643,196 A | 2/1987 | Tanaka et al. | |
| 4,696,287 A | 9/1987 | Hortmann et al. | |
| 4,795,995 A | 1/1989 | Eccleston | |
| 4,799,495 A | 1/1989 | Hawkins | |
| 4,909,789 A | 3/1990 | Taguchi et al. | |
| 4,936,823 A | 6/1990 | Colvin et al. | |
| 4,945,914 A | 8/1990 | Allen | |
| 4,994,079 A | 2/1991 | Genese | |
| 5,018,178 A | 5/1991 | Katsumata et al. | |
| 5,031,634 A | 7/1991 | Simon | |
| 5,062,847 A | 11/1991 | Barnes | |
| 5,095,224 A | 3/1992 | Renger | |
| 5,099,845 A | 3/1992 | Besz et al. | |
| 5,107,862 A | 4/1992 | Fabian et al. | |
| 5,142,292 A | 8/1992 | Chang | |
| 5,170,055 A | 12/1992 | Carroll et al. | |
| 5,325,873 A | 7/1994 | Hirschi et al. | |
| 5,353,804 A | 10/1994 | Kornberg et al. | |
| 5,409,004 A | 4/1995 | Sloan | |
| 5,423,334 A | 6/1995 | Jordan | |
| 5,425,367 A | 6/1995 | Shapiro | |
| 5,425,382 A | 6/1995 | Golden et al. | |
| 5,446,548 A * | 8/1995 | Gerig et al. | 356/620 |
| 5,509,900 A | 4/1996 | Kirkman | |
| 5,528,651 A | 6/1996 | Leksell | |
| 5,626,630 A * | 5/1997 | Markowitz et al. | 607/60 |
| 5,638,819 A | 6/1997 | Manwaring et al. | |
| 5,651,043 A | 7/1997 | Tsuyuki et al. | |
| 5,680,106 A | 10/1997 | Schrott | |
| 5,697,384 A | 12/1997 | Miyawaki et al. | |
| 5,707,362 A | 1/1998 | Yoon | |
| 5,707,390 A | 1/1998 | Bonutti | |
| 5,711,299 A * | 1/1998 | Manwaring et al. | 600/417 |
| 5,727,552 A | 3/1998 | Ryan | |
| 5,735,795 A | 4/1998 | Young et al. | |
| 5,748,767 A * | 5/1998 | Raab | 382/128 |
| 5,754,623 A | 5/1998 | Seki et al. | |
| 5,757,881 A | 5/1998 | Hughes | |
| 5,764,052 A | 6/1998 | Renger | |
| 5,769,861 A | 6/1998 | Vilsmeier | |
| 5,810,851 A | 9/1998 | Yoon | |
| 5,815,076 A | 9/1998 | Herring | |
| 5,840,148 A | 11/1998 | Campbell | |
| 5,868,673 A | 2/1999 | Vesely | |
| 5,879,297 A | 3/1999 | Haynor et al. | |
| 5,910,144 A | 6/1999 | Hayashi | |
| 5,928,137 A | 7/1999 | Green et al. | |
| 5,951,481 A | 9/1999 | Evans | |
| 5,957,934 A | 9/1999 | Rapoport et al. | |
| 5,989,265 A | 11/1999 | Bouquet De La Joliniere et al. | |
| 6,026,818 A | 2/2000 | Blair | |
| 6,031,533 A | 2/2000 | Peddada et al. | |
| 6,059,734 A | 5/2000 | Yoon | |
| 6,061,644 A | 5/2000 | Leis | |
| 6,067,465 A | 5/2000 | Foo | |
| 6,076,008 A | 6/2000 | Bucholz | |
| 6,081,238 A | 6/2000 | Alicot | |
| 6,082,366 A | 7/2000 | Andra et al. | |
| 6,144,875 A | 11/2000 | Schweikard et al. | |
| 6,161,009 A | 12/2000 | Skurdal et al. | |
| 6,198,963 B1 | 3/2001 | Haim et al. | |
| 6,222,544 B1 * | 4/2001 | Tarr et al. | 715/839 |
| 6,246,900 B1 | 6/2001 | Cosman et al. | |
| 6,307,473 B1 | 10/2001 | Zampini et al. | |
| 6,325,758 B1 | 12/2001 | Carol et al. | |
| 6,353,655 B1 | 3/2002 | Siochi | |
| 6,359,959 B1 | 3/2002 | Butler et al. | |
| 6,360,116 B1 * | 3/2002 | Jackson et al. | 600/427 |
| 6,363,940 B1 | 4/2002 | Krag | |
| 6,371,379 B1 | 4/2002 | Dames | |
| 6,377,162 B1 * | 4/2002 | Delestienne et al. | 340/286.07 |
| 6,381,485 B1 | 4/2002 | Hunter et al. | |
| 6,385,286 B1 | 5/2002 | Fitchard et al. | |
| 6,385,288 B1 | 5/2002 | Kanematsu | |
| 6,393,096 B1 | 5/2002 | Carol et al. | |
| 6,405,072 B1 | 6/2002 | Cosman | |
| 6,416,520 B1 | 7/2002 | Kynast et al. | |
| 6,501,981 B1 | 12/2002 | Schweikard et al. | |
| 6,510,199 B1 | 1/2003 | Hughes et al. | |
| 6,526,415 B2 | 2/2003 | Smith et al. | |
| 6,535,756 B1 | 3/2003 | Simon et al. | |
| 6,650,930 B2 | 11/2003 | Ding et al. | |
| 6,662,036 B2 | 12/2003 | Cosman | |
| 6,675,810 B2 | 1/2004 | Krag | |
| 6,698,433 B2 | 3/2004 | Krag | |
| 6,711,431 B2 | 3/2004 | Sarin et al. | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,882,947 B2 | 4/2005 | Levin | |
| 6,889,833 B2 | 5/2005 | Seiler et al. | |
| 6,918,919 B2 | 7/2005 | Krag | |
| 6,934,356 B1 | 8/2005 | Satheesan et al. | |
| 6,937,696 B1 | 8/2005 | Mostafavi | |
| 6,977,504 B2 | 12/2005 | Wright et al. | |
| 6,993,112 B2 | 1/2006 | Hesse et al. | |
| 6,999,555 B2 | 2/2006 | Morf et al. | |
| 7,026,927 B2 | 4/2006 | Wright et al. | |
| 7,027,707 B2 | 4/2006 | Imaki et al. | |
| 7,072,707 B2 | 7/2006 | Galloway, Jr. et al. | |
| 7,142,905 B2 | 11/2006 | Slayton et al. | |
| 7,154,991 B2 | 12/2006 | Earnst et al. | |
| 7,174,201 B2 | 2/2007 | Govari et al. | |
| 7,176,798 B2 | 2/2007 | Dimmer et al. | |
| 7,206,626 B2 | 4/2007 | Quaid, III | |
| 7,206,627 B2 | 4/2007 | Abovitz et al. | |
| 7,213,009 B2 | 5/2007 | Pestotnik et al. | |
| 7,221,733 B1 | 5/2007 | Takai et al. | |
| 7,280,863 B2 | 10/2007 | Shacher | |
| 7,289,599 B2 | 10/2007 | Seppi et al. | |
| 7,289,839 B2 | 10/2007 | Dimmer et al. | |
| 7,318,805 B2 | 1/2008 | Schweikard et al. | |
| 7,351,208 B2 | 4/2008 | Brodnick et al. | |
| 7,447,643 B1 | 11/2008 | Olson et al. | |
| 7,587,234 B2 | 9/2009 | Owens et al. | |
| 7,606,405 B2 | 10/2009 | Sawyer et al. | |
| 7,657,301 B2 | 2/2010 | Mate et al. | |
| 7,657,302 B2 | 2/2010 | Mate et al. | |
| 7,657,303 B2 | 2/2010 | Mate et al. | |
| 7,684,849 B2 | 3/2010 | Wright et al. | |
| 7,912,529 B2 | 3/2011 | Herron et al. | |
| 8,239,002 B2 | 8/2012 | Neustadter et al. | |
| 8,239,005 B2 | 8/2012 | Wright et al. | |
| 2002/0049362 A1 | 4/2002 | Ding | |
| 2002/0065461 A1 | 5/2002 | Cosman | |
| 2002/0083951 A1 | 7/2002 | Stegmaier et al. | |
| 2002/0165443 A1 | 11/2002 | Mori | |
| 2002/0188194 A1 | 12/2002 | Cosman | |
| 2002/0193685 A1 | 12/2002 | Mate | |
| 2002/0193686 A1 * | 12/2002 | Gilboa | 600/424 |
| 2003/0002621 A1 | 1/2003 | Hughes et al. | |
| 2003/0023161 A1 * | 1/2003 | Govari et al. | 600/423 |
| 2003/0052785 A1 | 3/2003 | Gisselberg | |
| 2003/0088178 A1 | 5/2003 | Owens et al. | |
| 2003/0125616 A1 | 7/2003 | Black et al. | |
| 2003/0153829 A1 | 8/2003 | Sarin et al. | |
| 2003/0192557 A1 | 10/2003 | Krag | |
| 2003/0206610 A1 | 11/2003 | Collins | |
| 2003/0206614 A1 | 11/2003 | Kendrick et al. | |
| 2004/0019274 A1 | 1/2004 | Galloway et al. | |
| 2004/0068182 A1 | 4/2004 | Misra | |
| 2004/0096033 A1 | 5/2004 | Seppi et al. | |
| 2004/0116804 A1 | 6/2004 | Mostafavi | |
| 2004/0122308 A1 | 6/2004 | Ding | |
| 2004/0122311 A1 | 6/2004 | Cosman | |
| 2004/0122608 A1 | 6/2004 | Levin | |
| 2004/0125916 A1 | 7/2004 | Herron et al. | |
| 2004/0127787 A1 | 7/2004 | Dimmer et al. | |
| 2004/0133101 A1 | 7/2004 | Mate et al. | |
| 2004/0133887 A1 | 7/2004 | Herle et al. | |
| 2004/0138555 A1 | 7/2004 | Krag | |
| 2004/0158146 A1 | 8/2004 | Mate et al. | |
| 2004/0176931 A1 | 9/2004 | Wright et al. | |
| 2005/0059884 A1 | 3/2005 | Krag | |

(56) References Cited

U.S. PATENT DOCUMENTS

| | | |
|---|---|---|
| 2005/0059887 A1 | 3/2005 | Mostafavi et al. |
| 2005/0077459 A1 | 4/2005 | Engler et al. |
| 2005/0085710 A1 | 4/2005 | Earnst et al. |
| 2005/0113855 A1 | 5/2005 | Kennedy et al. |
| 2005/0144139 A1 | 6/2005 | Zhuge et al. |
| 2005/0151649 A1 | 7/2005 | Wright et al. |
| 2005/0152495 A1 | 7/2005 | Hesse |
| 2005/0154280 A1 | 7/2005 | Wright et al. |
| 2005/0154283 A1 | 7/2005 | Wright et al. |
| 2005/0154284 A1 | 7/2005 | Wright et al. |
| 2005/0154293 A1 | 7/2005 | Gisselberg |
| 2005/0195084 A1 | 9/2005 | Dimmer |
| 2005/0234332 A1 | 10/2005 | Murphy |
| 2005/0261570 A1 | 11/2005 | Mate et al. |
| 2006/0052694 A1 | 3/2006 | Phillips et al. |
| 2006/0058648 A1 | 3/2006 | Meier et al. |
| 2006/0063999 A1 | 3/2006 | Herron et al. |
| 2006/0074301 A1 | 4/2006 | Meier et al. |
| 2006/0074302 A1 | 4/2006 | Meier et al. |
| 2006/0078086 A1 | 4/2006 | Riley et al. |
| 2006/0079764 A1 | 4/2006 | Wright et al. |
| 2006/0093089 A1 | 5/2006 | Vertatschitsch et al. |
| 2006/0100509 A1 | 5/2006 | Wright et al. |
| 2007/0161884 A1 | 7/2007 | Black et al. |
| 2008/0226149 A1 | 9/2008 | Wischmann et al. |

FOREIGN PATENT DOCUMENTS

| | | |
|---|---|---|
| FR | 26335259 | 2/1990 |
| FR | 2686499 | 7/1993 |
| JP | 07313515 A | 12/1995 |
| JP | 8-166446 | 6/1996 |
| JP | 2001008947 A | 1/2001 |
| JP | 2004154548 A | 6/2004 |
| WO | WO-95/25475 | 9/1995 |
| WO | 9608208 A1 | 3/1996 |
| WO | WO-97/12553 | 4/1997 |
| WO | WO-98/30166 | 7/1998 |
| WO | WO-98/38908 | 9/1998 |
| WO | WO-98/40026 A | 9/1998 |
| WO | 9927839 A2 | 6/1999 |
| WO | WO-99/30182 | 6/1999 |
| WO | WO-99/33406 | 7/1999 |
| WO | WO-99/40869 | 8/1999 |
| WO | WO-99/58044 | 11/1999 |
| WO | WO-99/58065 | 11/1999 |
| WO | WO-00/38579 | 7/2000 |
| WO | WO-00/51514 | 9/2000 |
| WO | WO-00/53115 | 9/2000 |
| WO | WO-00/65989 A | 11/2000 |
| WO | WO-02/39917 | 5/2002 |
| WO | WO-02/39918 | 5/2002 |
| WO | WO-0239918 | 5/2002 |
| WO | 03053270 A2 | 7/2003 |

OTHER PUBLICATIONS

U.S. Appl. No. 60/590,693, filed Jul. 23, 2004, Wright et al.
U.S. Appl. No. 60/590,697, filed Jul. 23, 2004, Phillips et al.
U.S. Appl. No. 60/590,699, filed Jul. 23, 2004, Herron et al.
U.S. Appl. No. 09/877,498, filed Jun. 8, 2001, Mate et al.
Beyer, et al., Beyer, Thomas et al. "Dual-modality PET/CT Imaging: the effect of respiratory motion on combined image quality in clinical oncology." European journal of nuclear medicine and molecular imaging 30.4 (2003): 588-596.
Low, Daniel A. et al., Low, Daniel A., et al. "A method for the reconstruction of four-dimensional synchronized CT scans acquired during free breathing." Medical physics 30.6 (2003) 1254-1263.
Seiler, P. G. et al., P.G. Seiler, et al., A novel tracking technique for the continuous precise measurement of tumour positions in confomral therapy, Jun. 7, 2000, IOP Publishing Ltd., Phys. Med. Biol., vol. 45, pp. N103-N110.
Seppenwoolde, et al., Seppenwoolde et al, Precise and real-time measurement of 3D tumor motion in lung due to breathing and heartbeat, measured during radiotherapy, Int. J. Radiat. Oncol. Biol. Phys. Jul. 15, 2002, 53, pp. 822-34.
Sharpe, et al., Sharp et al., Prediction of Respiratory Tumour Motion for Real-Time Image-Guided Radiotherapy, IPO Publishing Oltd.; Jan. 16, 2004, pp. 425-440.
Wolthaus, J.W. H. et al., Wolthaus, J. W. H., et al. "Fusion of respiration-correlated PET and CT scans: correlated lung tumour motion in anatomical and functional scans." Physics in medicine and biology 50.7 (2005): 1569.

\* cited by examiner

New Patient

Page 1 of 4 – Patient demographics

Enter the patient name and ID.
Required fields are marked with an asterisk (*). — 2301

*First — 2302
MI — 2303
*Last — 2304
*Patient ID — 2305

< Back   Next > — 2392    Cancel — 2393

*FIG. 23*

New Patient – Harold T Stone (ID: 372-03-9373) ☒

Page 2 of 4 – Calypso localization plan information

Enter the Calypso localization plan information. — 2401
Required fields are marked with an asterisk (*).

| | | |
|---|---|---|
| *Usage mode | ⦿ Localized and track<br>○ Localize only  ☐ Record tracking sample | 2402 |

*Implantation date  [6/10/2004 ▼] — 2403

|  | Lateral | Longitudinal | Vertical |
|---|---|---|---|
| *Upper tracking limit | [0.5] cm | [0.5] cm | [0.5] cm |
| *Lower tracking limit | [0.5] cm | [0.5] cm | [0.5] cm |

— 2404

Physician [Harold Lomb ▼] — 2405
Dosimetrist [Joe Waltrew ▼] — 2406
Physicist [Donald Horton ▼] — 2407

[< Back] — 2491    [Next >] — 2492    [Cancel] — 2493

*FIG. 24*

Edit Patient – David K Parker (ID: 109-05-6358) ☒ ─ 2600

Page 4 of 4 – Summary

Verify the displayed patient and Calypso localization plan information.
Click "Apply Changes" to save the data.
Required fields are marked with an asterisk (*). ─ 2601

*Patient Name [David K Parker] ─ 2602
*Patient ID [109-05-6358] ─ 2603
*Usage mode [LocalizeOnly] ─ 2604
*Implantation date [2/26/2004] ─ 2605
Physician [Dr. Julia Vosk] ─ 2606
Dosimetrist [Susan Warren] ─ 2607
Physicist [Nancy Donaldson] ─ 2608

| | Lateral | Longitudinal | Vertical |
|---|---|---|---|
| *Upper tracking limit | [0.5] cm | [0.5] cm | [0.5] cm |
| *Lower tracking limit | [0.5] cm | [0.5] cm | [0.5] cm |

⎫ 2609

| | X | Y | Z |
|---|---|---|---|
| *Treatment isocenter | [100.0] mm | [200.0] mm | [300.0] mm | ⎬ 2610
| *Apex | [100.0] mm | [200.0] mm | [280.0] mm |
| *Left mid-base | [80.0] mm | [200.0] mm | [320.0] mm | ⎬ 2611
| *Right mid-base | [120.0] mm | [200.0] mm | [320.0] mm |

*Input CRF [Varian Eclipse] ─ 2612
*Patient orientation [Prone] ─ 2613
*Geometric residual limit [2.00] cm ─ 2614
*Rotational alignment limit [35] degrees ─ 2615

[Overrides approved]

[< Back] ─ 2691   [Apply Changes] ─ 2694   [Cancel] ─ 2693

*FIG. 26*

Edit Patient

Page 1 of 4 — Patient demographics

Enter the patient name.
Required fields are marked with an asterisk (*). — 2701

- *First: Leonard — 2702
- MI: H — 2703
- *Last: Iverson — 2704
- *Patient ID: 552-51-9905 — 2705

[ < Back ]  [ Next > ]   [ Cancel ]

USER INTERFACE FOR GUIDED RADIATION THERAPY

CROSS-REFERENCE TO RELATED APPLICATIONS

This application claims the benefit of U.S. Patent Application No. 60/590,699 filed Jul. 23, 2004, which is hereby incorporated by reference in its entirety.

TECHNICAL FIELD

The present invention is directed to the field of visual user interfaces relating to medical applications.

BACKGROUND

Radiation therapy can be used to treat localized cancer. In a typical application, a radiation delivery system has an ionizing radiation device mounted to a movable gantry. The radiation delivery system controls the motion of the radiation device to direct an ionizing radiation beam to a specific point in space commonly referred to as the "machine isocenter." One aspect of radiation therapy is positioning a patient so that the patient's tumor is located at the machine isocenter throughout treatment. Patient positioning systems use various technologies to locate the tumor, including optically locating visual markers applied to the patient's skin, or using X-ray analysis to locate metal fiducials subcutaneously implanted in the patient.

It is typical for attendants such as radiation therapists to perform tasks relating to radiation treatment, such as positioning the patient for treatment, setting up aspects of the patient positioning system, and monitoring the output of the patient positioning system to ensure that the patient remains properly positioned throughout treatment.

A patient positioning system that provided information likely to assist the attendants in their tasks in a manner that is clear and easy to understand would have significant utility.

BRIEF DESCRIPTION OF THE DRAWINGS

FIG. 23 is a display diagram showing a sample first display presented by the facility for the patient wizard.

FIG. 24 is a display diagram showing a sample second display presented by the facility for the patient wizard.

FIG. 26 is a display diagram showing a sample fourth display presented by the facility for the patient wizard.

FIG. 27 is a display diagram showing a sample first display presented by the facility for the patient wizard in the edit mode.

FIG. 28 is a display diagram showing a sample second display presented by the facility for the patient wizard in the edit mode.

DETAILED DESCRIPTION

A software facility for providing a visual user interface ("UI") (a) for guided radiation therapy and/or (b) in connection with a patient tracking system for radiation therapy ("the facility") is described. The UI is designed to assist users such as attendants in a radiation therapy facility—e.g., radiation therapy technicians—with such tasks as selecting and setting up a patient; monitoring a patient's position; testing the accuracy of a patient tracking system, such as a patient tracking system using passive magnetic transponders; and calibrating an optical alignment system for aligning a patient tracking system sensor, such as a magnetic excitation and sensor array.

In some embodiments, the facility displays the UI in accordance with a "wizard" paradigm, in which the user is directed through a sequence of steps by displaying a corresponding sequence of screens, and tracking the user's progress through the sequence in a clear and consistent manner. In the description that follows, the steps of such sequences are sometimes referred to as "states" of the UI. One or more steps or states may collectively make up a "task" that is part of the sequence. In some embodiments, the facility ensures that each step of a sequence is performed before the user can advance to the next step. In some embodiments, the facility employs consistent visual elements for common concepts within and between different tasks. In some embodiments, the facility displays the same information simultaneously in two or more different forms, such as in numerical form and/or one or more graphical forms. In some embodiments, the facility displays important information in a large size to make it more readable from a distance. In some embodiments, the facility employs colors to impart meaning, such as whether a value is within tolerance. In some embodiments, the facility displays information received from sensors in real-time or in near-real-time to provide immediate feedback about the movement of a patient or tracking system sensor being tracked by the facility. In some embodiments, the facility displays information on one, some, all, or any of multiple display devices, that are each either inside or outside of a radiation treatment vault, or mobile between these two areas.

By presenting a UI in some or all of the manners discussed above, the facility enables radiation therapy facility attendants to swiftly and accurately perform tasks associated with the radiation therapy process.

Figure 1:
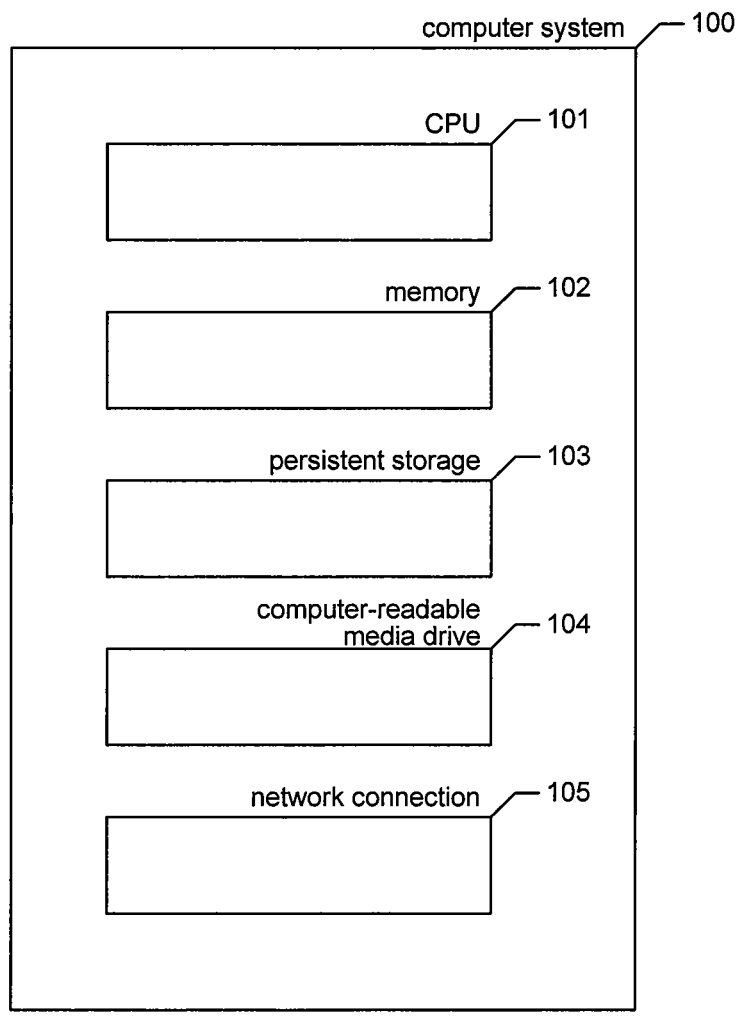
FIG. 1 is a block diagram showing some of the components typically incorporated in at least some of the computer systems and other devices on which the facility executes.

FIG. 1 is a block diagram showing some of the components typically incorporated in at least some of the computer systems and other devices on which the facility executes. These computer systems and devices 100 may include one or more central processing units ("CPUs") 101 for executing computer programs; a computer memory 102 for storing programs and data—including data structures—while they are being used; a persistent storage device 103, such as a hard drive, for persistently storing programs and data; a computer-readable media drive 104, such as a CD-ROM drive, for reading programs and data stored on a computer-readable medium; and a network connection 105 for connecting the computer system to other computer systems, such as via the Internet, to exchange programs and/or data—including data structures. While computer systems configured as described above are typically used to support the operation of the facility, one of ordinary skill in the art will appreciate that the facility may be implemented using devices of various types and configurations, and having various components.

In some embodiments, the user interfaces are implemented in the C# programming language using Microsoft Windows Forms. In some embodiments, the user interface receives information via the Microsoft .NET framework.

Figure 2:
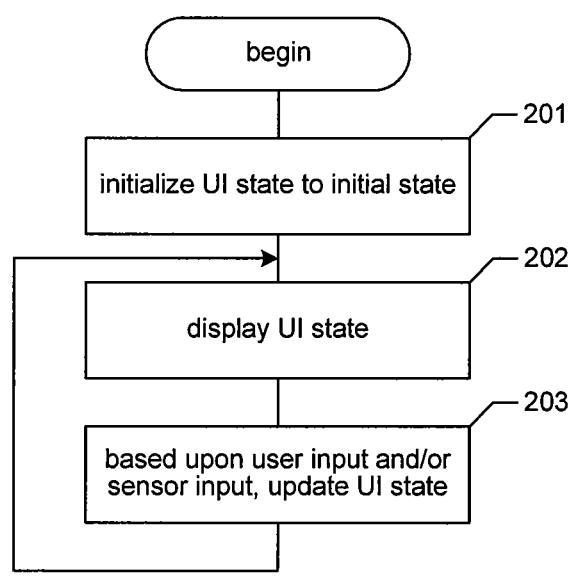
FIG. 2 is a flow diagram showing steps typically performed by the facility in order to present a user interface.

FIG. 2 is a flow diagram showing steps typically performed by the facility in order to present a user interface. In step 201, the facility initializes the UI to an initial state. In different embodiments, various initial states are used. In step 202, the facility displays the current UI state. In step 203, based upon user input and/or sensor input, the facility updates the current UI state. Updating the current UI state may include displaying a different screen, altering visual information presented on the current screen, etc. After step 203, the facility continues in step 202 to redisplay the current UI state.

In some embodiments, the facility presents the UI using hardware and/or software as described U.S. Patent Application No. 60/590,697 filed Jul. 23, 2004, entitled USER INTERFACE FOR GUIDED RADIATION THERAPY, and U.S. patent application Ser. No. 11/190194 entitled MODULAR SOFTWARE SYSTEM FOR GUIDED RADIATION THERAPY, filed concurrently herewith, each of which is hereby incorporated by reference in its entirety. One or more suitable, exemplary patient localization systems are described in the following, each of which is hereby incorporated by reference in its entirety: U.S. patent application Ser. No. 10/334,700, entitled PANEL-TYPE SENSOR/SOURCE ARRAY ASSEMBLY, filed Dec. 30, 2002; U.S. patent application Ser. No. 09/877,498, entitled GUIDED RADIATION THERAPY SYSTEM, filed Jun. 8, 2001; U.S. patent application Ser. No. 10/679,801, entitled METHOD AND SYSTEM FOR MARKER LOCALIZATION, filed Oct. 6, 2003; U.S. patent application Ser. No. 10/746,888, entitled IMPLANTABLE MARKER WITH WIRELESS SIGNAL TRANSMITTAL, filed Dec. 24, 2003; and U.S. patent application Ser. No. 10/749,478, entitled RECEIVER USED IN MARKER LOCALIZATION SENSING SYSTEM, filed Dec. 31, 2003.

Figure 3:
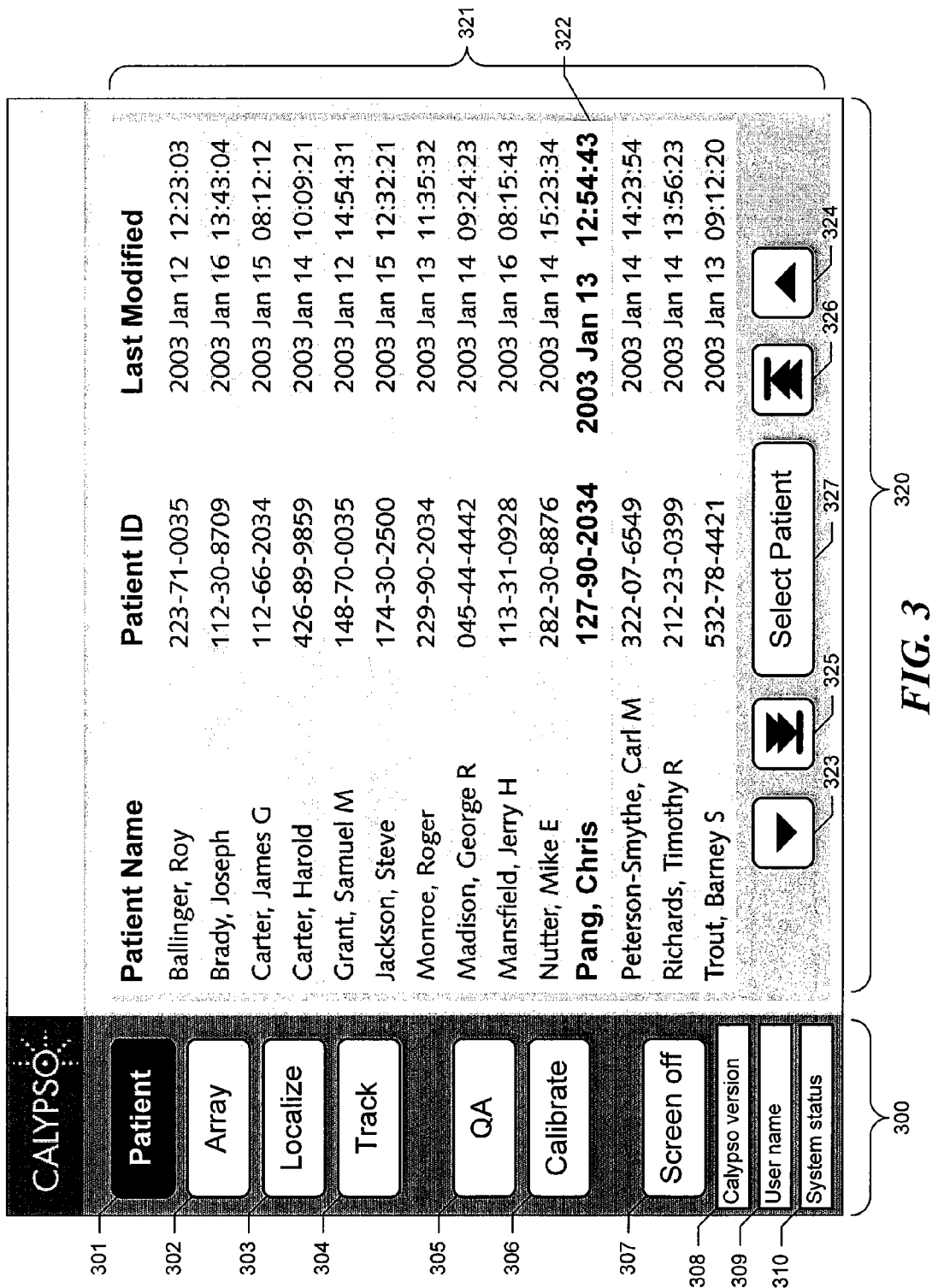
FIG. 3 is a display diagram showing a sample first display presented by the facility for the patient selection task.
Figure 4:
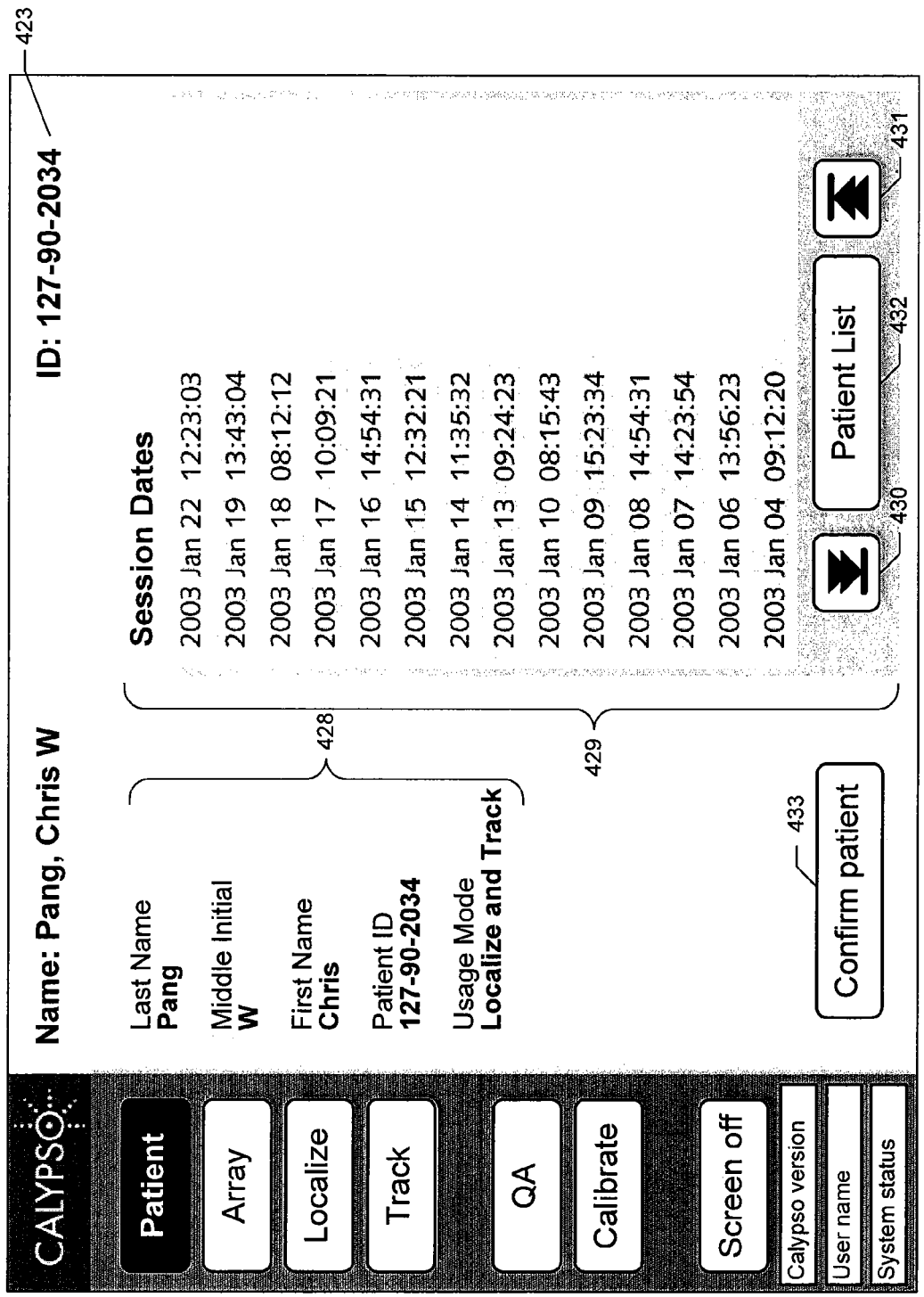
FIG. 4 is a display diagram showing a sample second display presented by the facility for the typical second display for the patient selection task.

FIG. 3-21 are display diagrams showing typical displays presented by the facility as part of the UI. FIGS. 3 and 4 show sample displays presented by the facility for the patient selection task. FIG. 3 is a display diagram showing a sample first display presented by the facility for the patient selection task. As part of the patient selection task, the user views a list of patients, selects a patient, and confirms the patient's information. FIG. 3, like most or all of the displays presented by the facility, contains a status panel 300. Typically, the status panel is displayed in the same location in each display in which it occurs, with consistent contents. The status panel contains a number of task indicators, such as indicator 301 for a patient selection task, indicator 302 for an array positioning task, indicator 303 for a patient localization task, indicator 304 for a patient location tracking task, indicator 305 for a patient tracking system quality assurance task, and an indicator 306 for an optical alignment system calibration task. In the status panel, a task indicator is visually distinguished, such as being displayed in different color or shading, to indicate that it is the current task—here, indicator 301 for the patient selection task is visually distinguished, indicating that it is the current task. Each of the indicators can typically be selected by the user—such as by using a touch screen or other pointing device—to select the corresponding task as the current task. The user may similarly select a screen off control 307 in order to switch off the display screen. The status panel may include other information, such as an indication 308 of one or more software versions, an indication 309 of the user's name, and an indication 310 of the status of the system.

In addition to the status panel, most displays presented by the facility include substantive contents 320. These substantive contents contain more detailed information about the task and/or step currently being performed. In the case of the patient selection task underway in FIG. 3, the additional contents include a list of patients 321 from which the user selects the patient to be treated. The user may choose a current patient by pointing to the patient in the list or by pointing to a down control 323 to move down one patient or an up control 324 to move up one patient. The user may also point to a scroll down control 325 to scroll down in the list or a scroll up control 326 to scroll up in the list. The user may choose a select patient control 327 to select the current patient.

FIG. 4 is a display diagram showing a sample second display presented by the facility for the patient selection task. FIG. 4 also shows the selected patient's name 423 at the top of the page. FIG. 4 also shows additional identifying information 428 for the patient. In a list 429 of past sessions for the current patient, the user can point to a scroll down control 430 to scroll down in the list of session dates or scroll up a control 431 to scroll up in the list of session dates. The user may point to a patient list control 432 to return to the display of FIG. 3, or may point to the confirm patient control 433 to confirm that the selected patient is the correct one.

Figure 5:
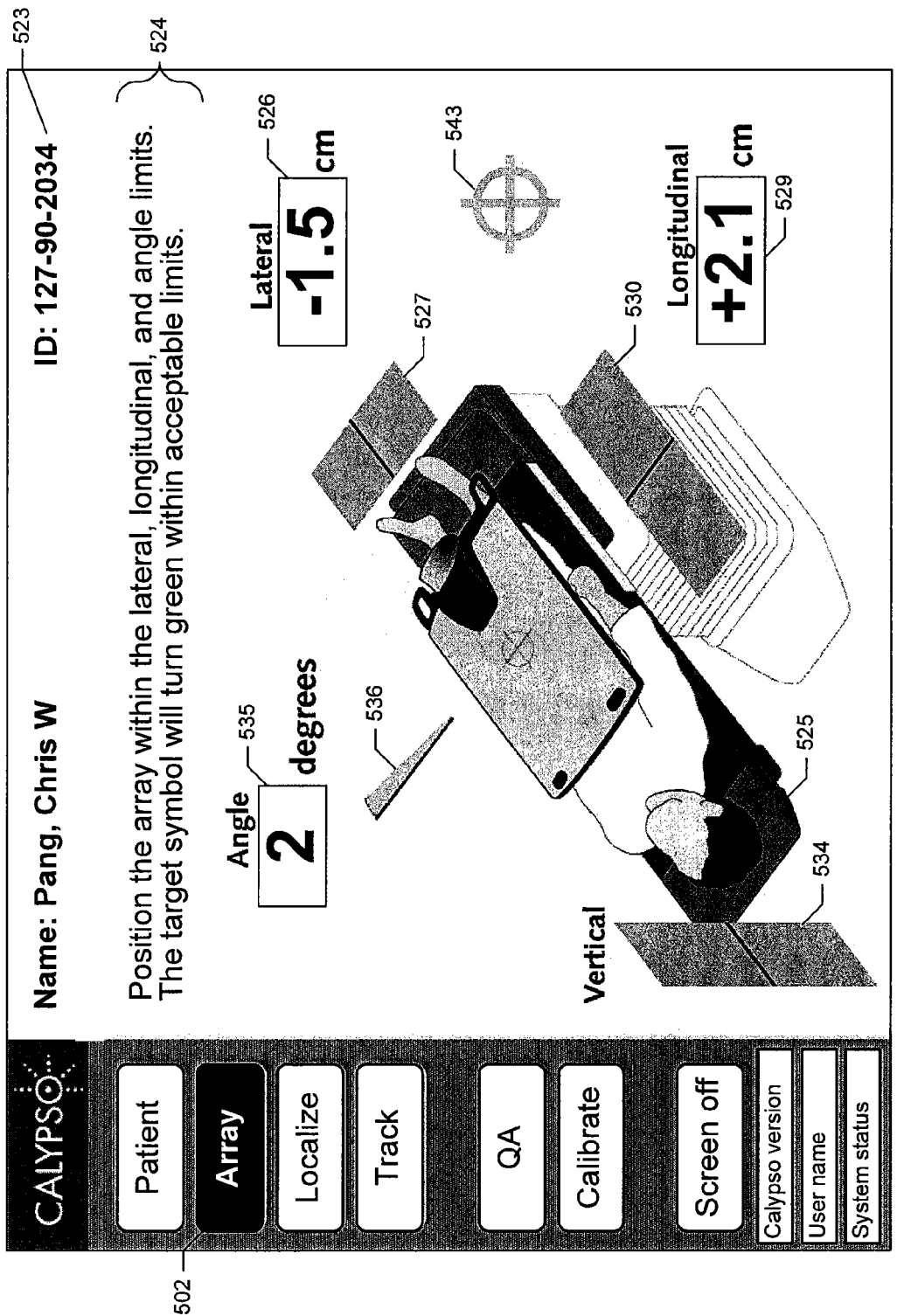
FIG. 5 is a display diagram showing a sample display presented by the facility as part of the array positioning task.

FIG. 5 is a display diagram showing a sample display presented by the facility as part of the array positioning task. As part of the array positioning task, the user positions a sensor array used by the patient tracking system within a predefined volume above the machine isocenter. To identify the array positioning task as the current task, the facility has visually distinguished the array positioning task indicator 502 in the status panel. FIG. 5 shows the patient's name 523, as well as instructions 524 directing the user on how to position a patient tracking sensor array relative to a patient and a patient table supporting the patient. The display includes a diagram 525 representing the patient table, the patient, and the array. The display includes information about the position of the array relative to the machine isocenter in three dimensions and in angular rotation: lateral, longitudinal, vertical, and the angular rotation of the sensor array about the vertical axis. For each of these three dimensions, the display includes a numerical indication of the deviation from ideal position or rotation, such as longitudinal numerical indication 529. Each numerical indication is typically displayed in a large, bold font, together with sign and units. Further, each numerical indication is typically displayed against the background color that indicates whether the corresponding value is within tolerance. The display of numerical longitudinal indication 529 against a background that is green rather than yellow indicates that the longitudinal position of the array is within tolerance. For each of the three dimensions and angular rotation, the display also includes a graphical indicator bar, such as longitudinal graphical indicator bar 530 that shows graphically how far the corresponding value deviates from optimal. Each graphical indicator bar is typically displayed in a color that indicates whether the corresponding value is within tolerance. Because the longitudinal graphical indicator bar 530 is displayed in green, rather than yellow, the longitudinal position of the array is within tolerance. All of the displayed position and rotation indicators are typically updated frequently to permit the user to reposition the sensor array relative to the machine isocenter, and receive prompt feedback on his or her progress. The display also includes a positioning success indicator 543, which indicates whether the array has been successfully positioned in all three dimensions. Because indicator 543 is displayed in green, rather than yellow, the array has been successfully positioned.

Figure 6:
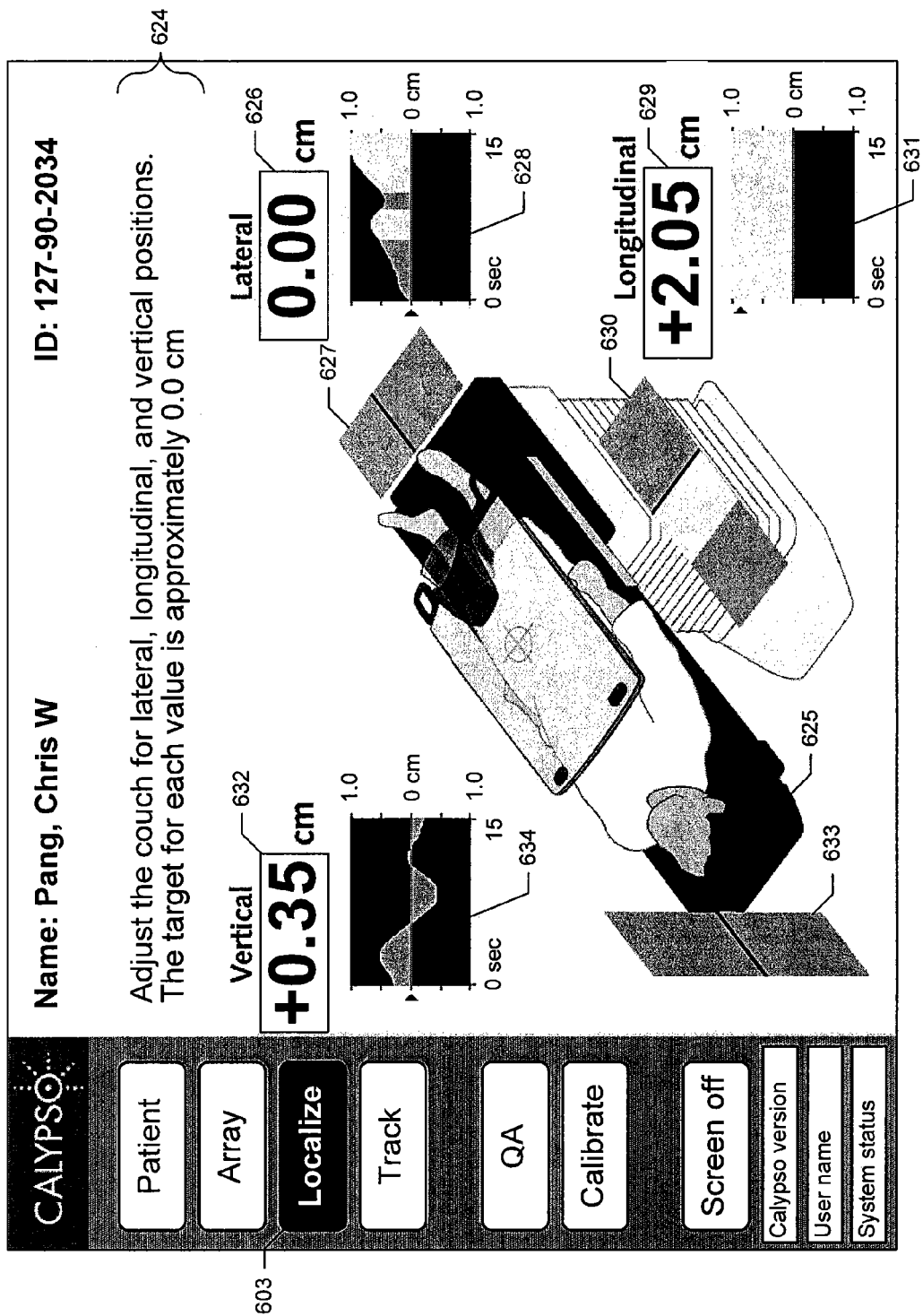
FIG. 6 is a display diagram showing a sample display presented by the facility for the patient localization task where the patient location is later to be tracked.
Figure 7:
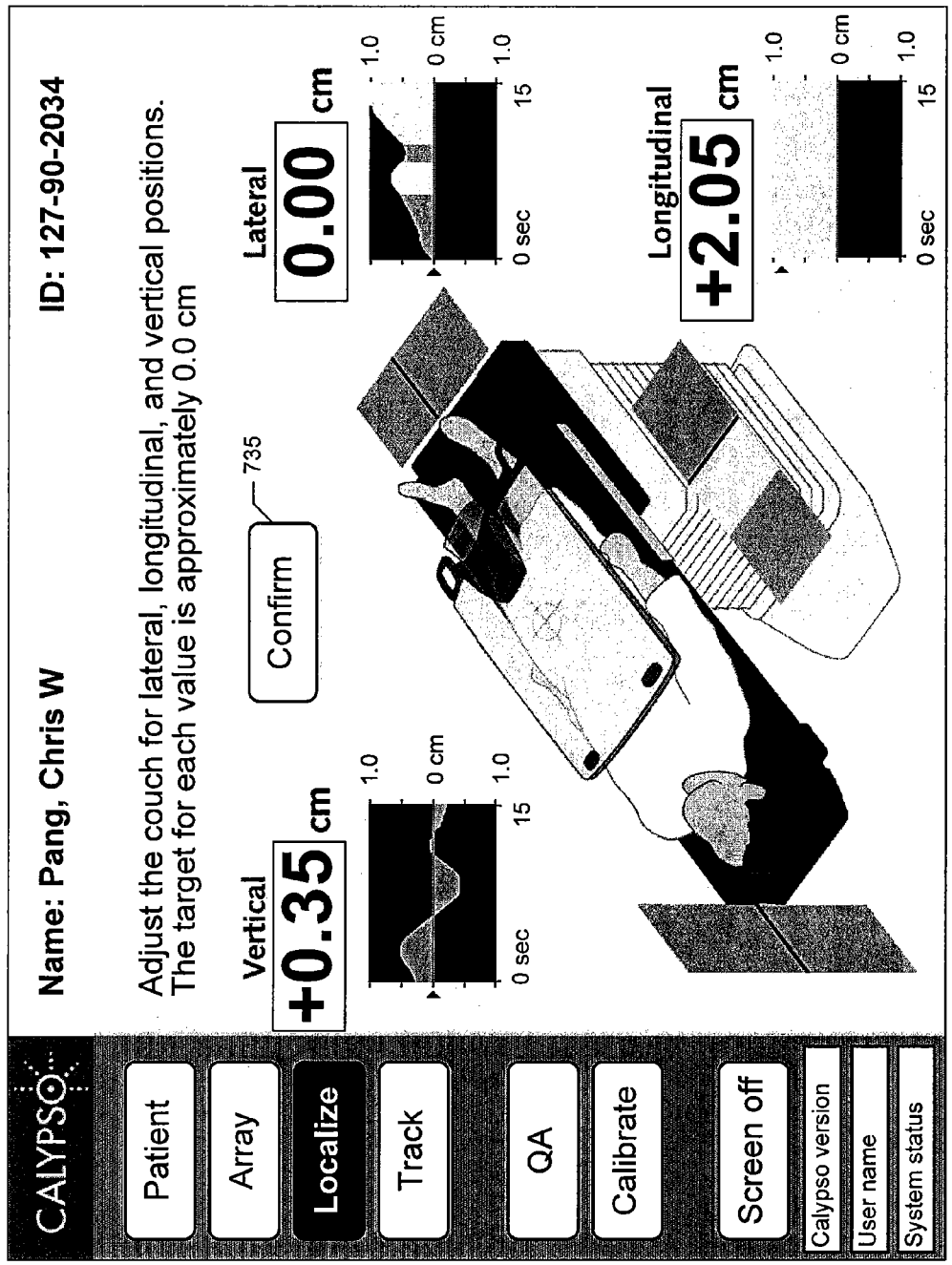
FIG. 7 is a display diagram showing a typical display presented by the facility for the patient localization task where the position in the patient is not later tracked.

FIGS. 6 and 7 show sample displays presented by the facility for the patient localization task. As part of the patient localization task, the user adjusts the vertical, longitudinal, and lateral position of the patient table to adjust for the offset between transponder positions and the treatment isocenter.

FIG. 6 is a display diagram showing a sample display presented by the facility for the patient localization task where the patient location is later to be tracked. Task indicator 603 is visually distinguished to indicate that the patient localization task is presently being performed. The display includes instructions 624 for moving the patient table to properly position the patient relative to the machine isocenter at which radiation will be delivered. The display also includes frequently-updated information obtained from the patient tracking system, such as the passive magnetic transponder localization system about the location of the treatment isocenter within the patient intended to receive radiation energy relative to the machine isocenter at which radiation will be delivered. This information is provided in three dimensions: lateral, longitudinal, and vertical. The information includes a numerical indication, such as longitudinal, numerical indication 629; a graphical indicator bar, such as longitudinal graphical indicator bar 630; and a time-distance graph, such as longitudinal time-distance graph 631. The time-distance graph indicates the position in the corresponding dimension over the course of time. The graphical indicator bars are typically not scaled, so that they provide consistent feedback over time and across patients and technicians. In some embodiments, the time-distance graphs are also not scaled. When a particular value is within tolerance, all three forms of indicators are displayed in a first color, such as blue (e.g., the vertical value). When a value for a particular dimension is outside of tolerance, it is displayed in a second color, such as yellow (e.g., the longitudinal value). In particular, each time-distance graph displays the value at times when it was within tolerance in the first color, and the times at which the value was out of tolerance in the second color (e.g., the lateral value). All of the displayed position indicators are typically updated frequently to permit the user to reposition the patient relative to the machine isocenter in order to align the treatment isocenter with the machine isocenter and receive prompt feedback on his or her progress.

FIG. 7 is a display diagram showing a typical display presented by the facility for the patient localization task where the position in the patient is not to be later tracked. FIG. 7 is similar to FIG. 6, except that a confirm control 735 is included in FIG. 7, which may be selected by the user to complete the patient localization task.

Figure 8:
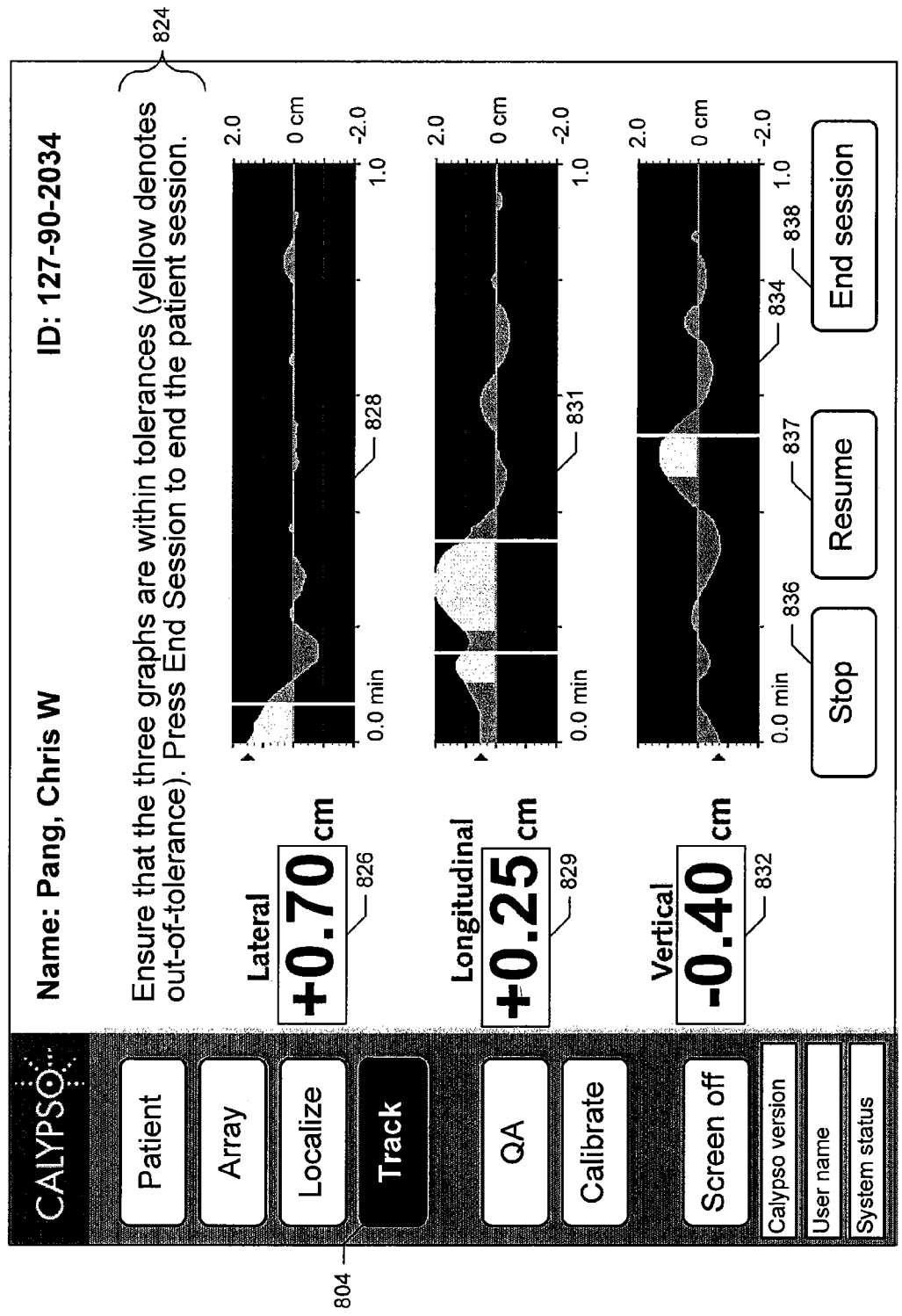
FIG. 8 is a display diagram showing a sample display presented by the facility for the patient location tracking task.

FIG. 8 is a display diagram showing a sample display presented by the facility for the patient location tracking task. As part of the patient location tracking task, the user monitors the treatment isocenter offset relative to the machine isocenter during the treatment session. Task indicator 804 has been visually distinguished to show that the patient location tracking task is the current task. FIG. 8 includes instructions 824 regarding this display. The display includes visual indicators for patient position in three dimensions: lateral, longitudinal, and vertical. For each of the three dimensions, the display includes both a numerical indicator, such as the lateral numerical indicator 826, and a time-distance graph, such as lateral time-distance graph 828. The display behavior of these indicators typically conforms to similar indicators shown and discussed above. The display also includes a stop control 836 for suspending the display and recording of patient position data; a resume control 837 for resuming display and recording after it is stopped; and an end session control 838 for ending the patient location tracking task and the patient's session.

Figure 9:
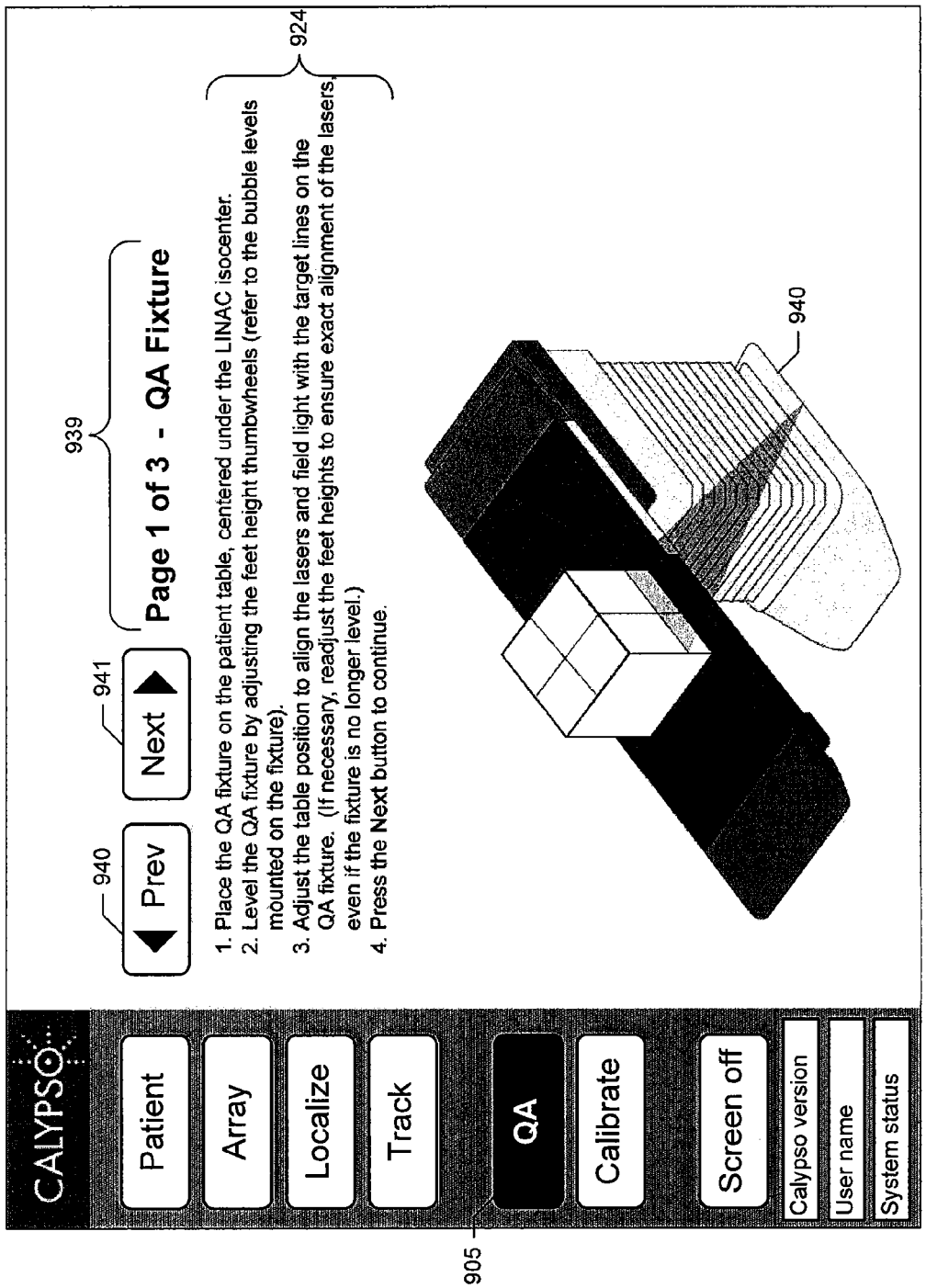
FIG. 9 is a display diagram showing a sample first display presented by the facility for the patient tracking system quality assurance task.
Figure 10:
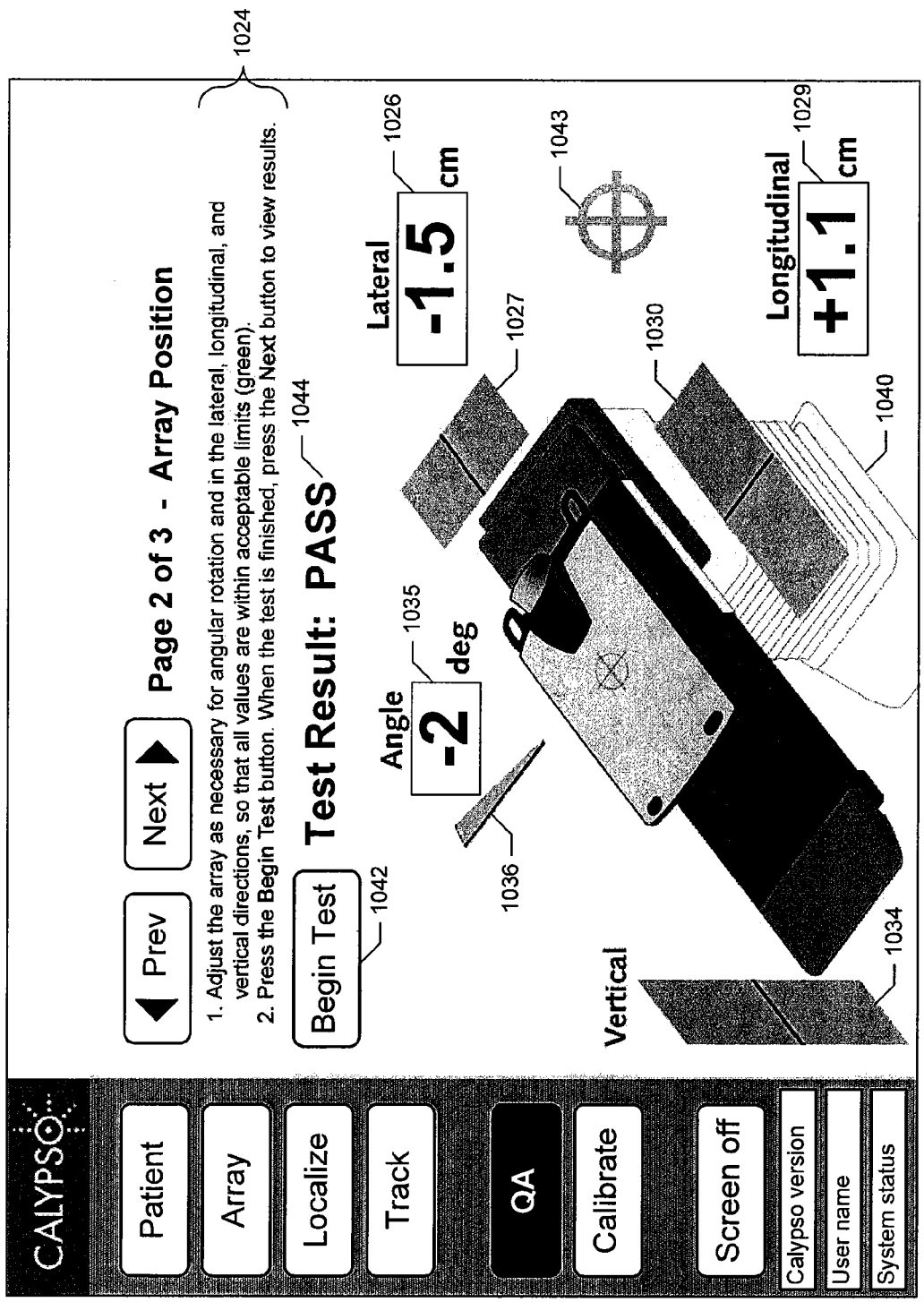
FIG. 10 is a display diagram showing a sample second display presented by the facility for the patient tracking system quality assurance task.
Figure 11:
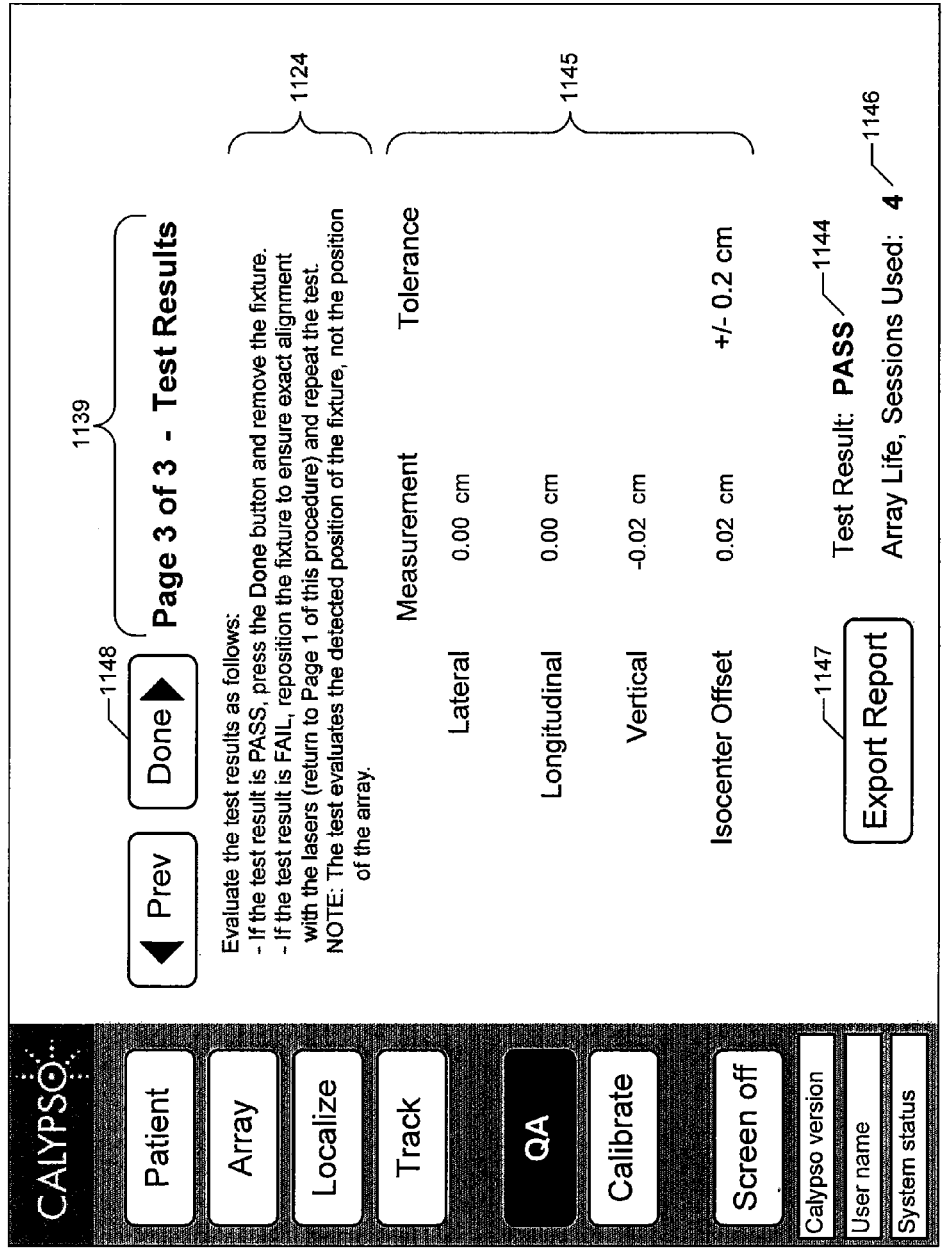
FIG. 11 is a display diagram showing a sample third display presented by the facility for the patient tracking system quality assurance task.

FIGS. 9-11 show sample displays presented by the facility for the patient tracking system quality assurance task. As part of the patient tracking system quality assurance task, the user tests the accuracy of the magnetic tracking subsystem, using a test fixture containing transponders in place of a patient in which transponders are implanted. FIG. 9 is a display diagram showing a sample first display presented by the facility for the patient tracking system quality assurance task. In FIG. 9, the quality assurance task indicator 905 is visually distinguished to indicate that the quality assurance task is the current task. FIG. 9 includes a page identifier 939 that helps the user to orient to his or her present position within the task. FIG. 9 includes a previous control 940 that the user may point to in order to move to a previous page for the task, and a next button 941 that the user may point to in order to move to the next page of the task. FIG. 9 includes instructions 924 for positioning a quality assurance fixture on the patient table. FIG. 9 further includes a diagram 940 showing the positioning of this equipment on the patient table.

FIG. 10 is a display diagram showing a second sample display presented by the facility in the quality assurance task. The page number indication 1039 reflects that the present display is in the second page of the quality assurance task. FIG. 10 includes instructions 1024 for positioning the sensor array and performing a quality assurance test of the patient tracking system. FIG. 10 includes numerical and graphical indicator bar indicators for the position of the array in each of three dimensions: lateral, longitudinal, and angle. FIG. 10 further includes an indicator 1043 indicating whether the array has been successfully positioned. FIG. 10 includes a begin test control 1042 that the user may point to after each array position dimension is within tolerance to begin a quality assurance test that detects and checks the transponders in the test fixture, then calculates a treatment isocenter offset and determines if the offset is within an expected tolerance. FIG. 10 further includes a test result indicator 1044 indicating the results of the test.

FIG. 11 is a display diagram showing a sample third display presented by the facility as part of a quality assurance task. The display includes instructions 1124 about how to act on the results of the test, as well as detailed results 1145, a result summary 1144, an array life indicator 1146, an export control 1147 that the user may point to in order to export the test results to a separate data store, and a done control 1148 that the user may point to in order to complete the quality assurance task.

Figure 12:
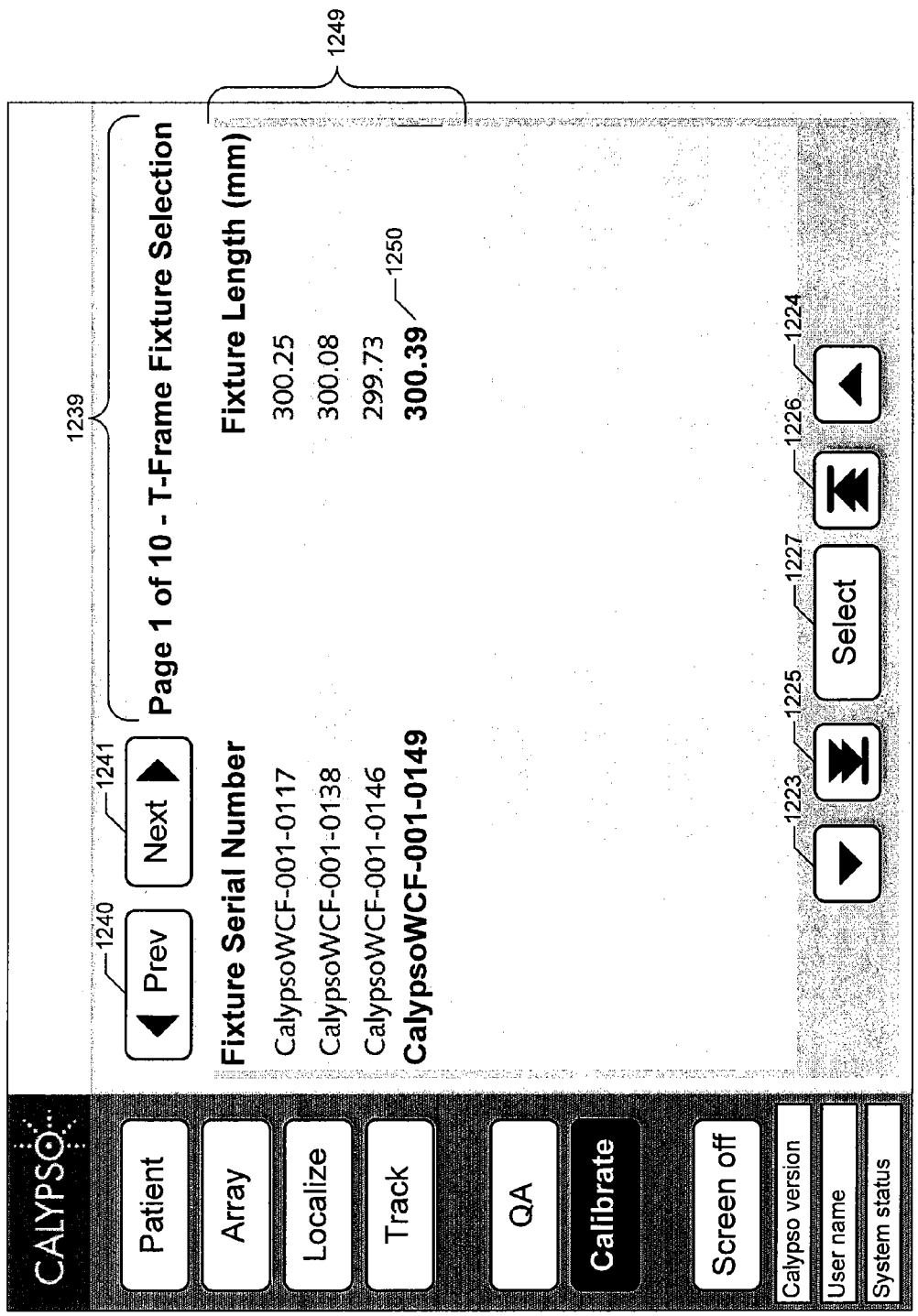
FIG. 12 is a display diagram showing a sample first display presented by the facility for the optical alignment system calibration task.

FIGS. 12-21 show sample displays presented by the facility for the optical alignment system calibration task. As part of the optical alignment system calibration task, the user calibrates the optical tracking and camera subsystems with respect to the machine isocenter. FIG. 12 is a display diagram showing a first display presented by the facility for the optical alignment system calibration task. FIG. 12 includes a page indicator 1239, and a list 1249 of T-Frame calibration fixtures. T-Frame calibration fixture 1250 is highlighted as the current T-Frame calibration fixture. The user may change the current T-Frame calibration fixture by pointing to a different T-Frame calibration fixture in the list, or by pointing to a down control 1223 to move down one calibration fixture or an up control 1224 to move up one T-Frame calibration fixture. The user may also point to a scroll down control 1225 to scroll down in the list of calibration fixtures or a scroll up control 1226 to scroll up in the list of T-Frame calibration fixtures. The user may point to a select control 1227 to select the current T-Frame calibration fixture.

Figure 13:
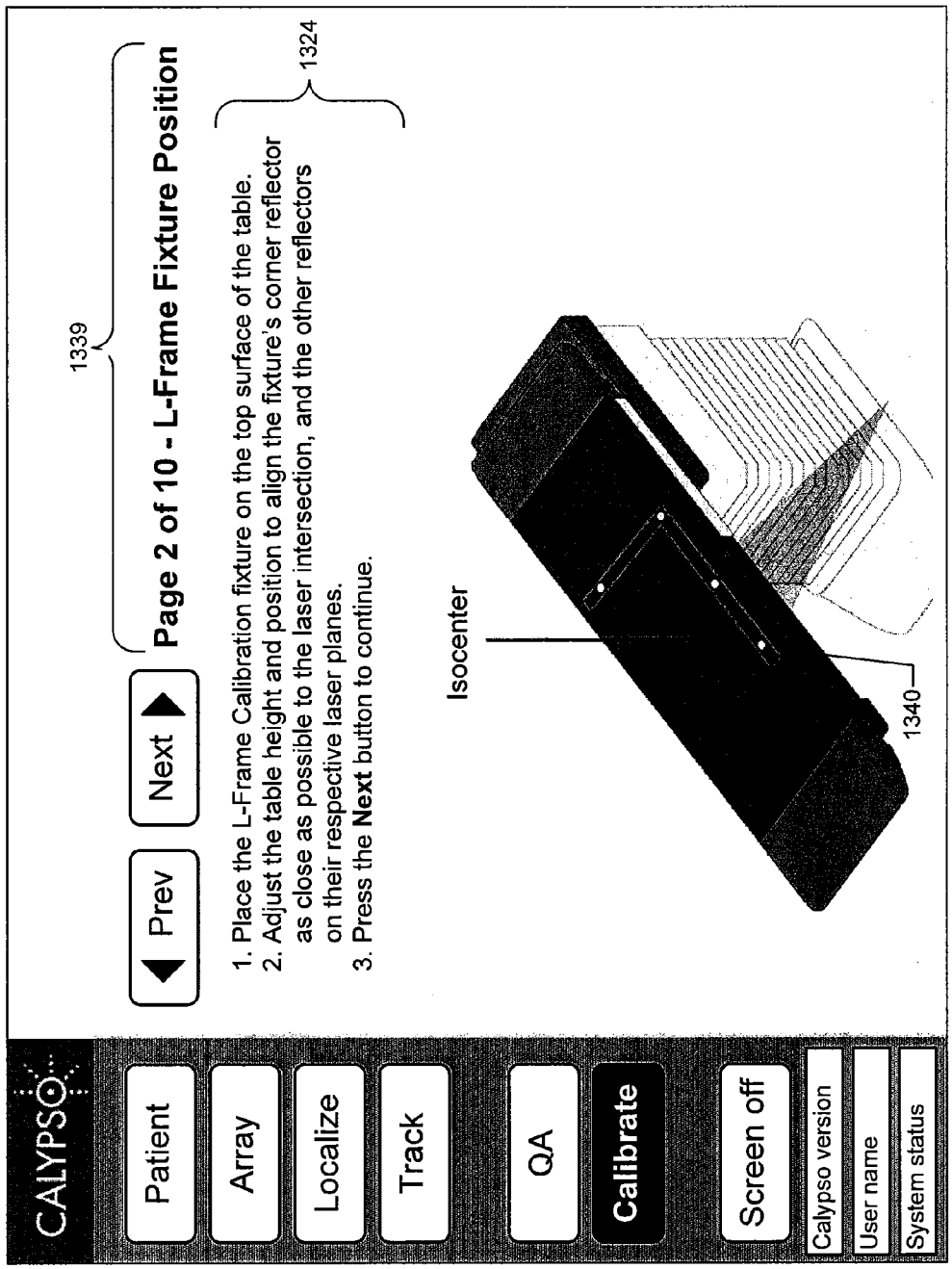
FIG. 13 is a display diagram showing a sample second display presented by the facility for the optical alignment system calibration task.

FIG. 13 is a display diagram showing a sample second display presented by the facility for the optical alignment system calibration task. FIG. 13 includes a page number indicator 1339, instructions 1324, and a diagram 1340 showing the positioning of an L-Frame calibration fixture on the patient table.

Figure 14:
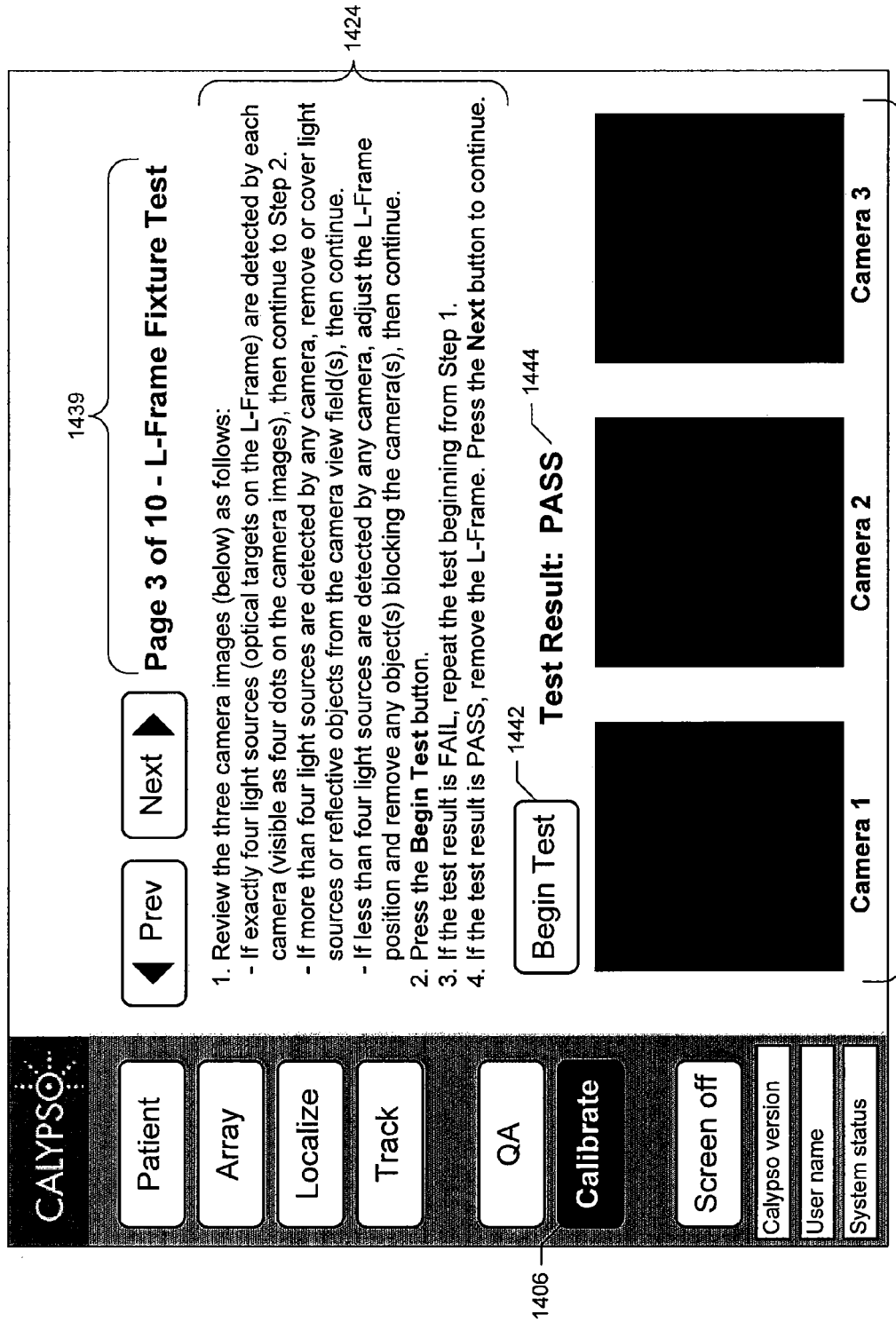
FIG. 14 is a display diagram showing a sample third display presented by the facility for the optical alignment system calibration task.

FIG. 14 is a display diagram showing a sample third display presented by the facility for the optical alignment system calibration task. FIG. 14 includes a page number indicator 1439 and instructions 1424. FIG. 14 further includes a begin test control 1444 that the user may point to in order to begin a camera test, and camera windows 1451 for displaying frames from each of the three cameras. FIG. 14 further includes a test result indicator 1444 indicating the result of the task.

Figure 15:
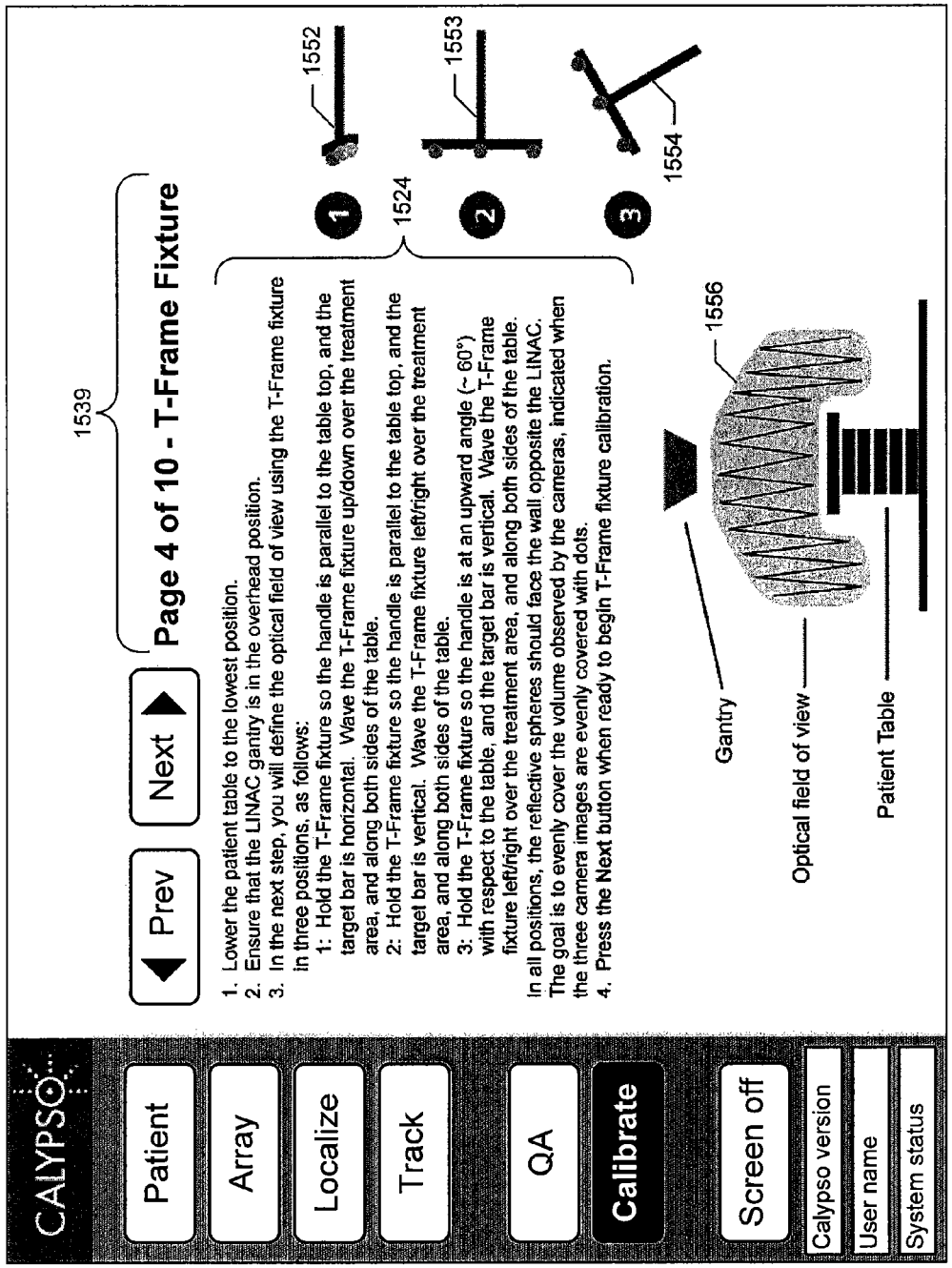
FIG. 15 is a display diagram showing a sample fourth display presented by the facility for the optical alignment system calibration task.

FIG. 15 is a display diagram showing a typical fourth display presented by the facility as part of a calibrate task. FIG. 15 includes a page number indicator 1539 and instructions 1524 regarding the placement of T-Frame calibration fixtures. FIG. 15 also includes diagrams 1552-1554 showing different orientations of T-Frame calibration fixtures, and diagram 1556 mapping the optical field of view through which T-Frame calibration fixtures are to be moved.

Figure 16:
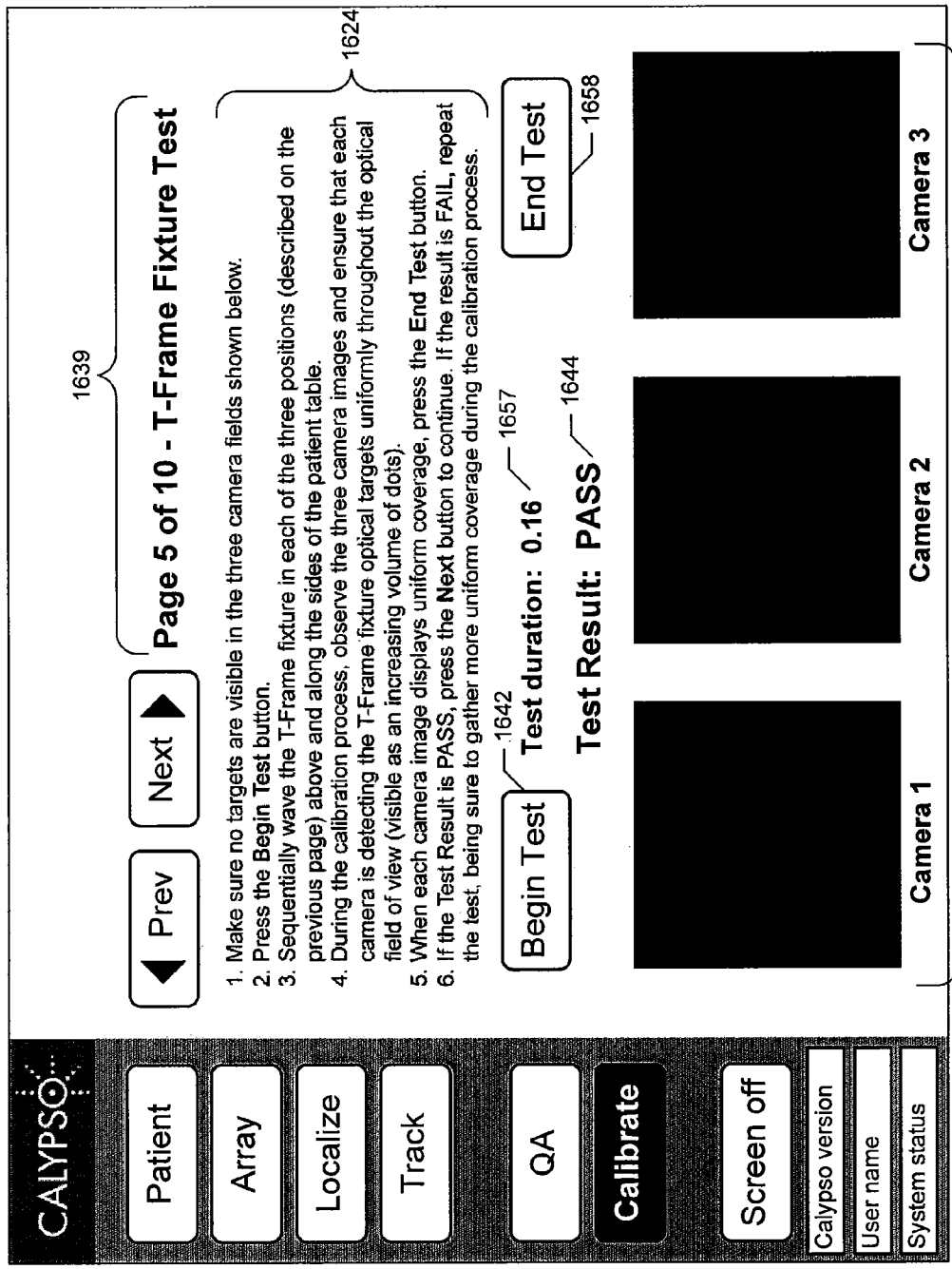
FIG. 16 is a display diagram showing a sample fifth display presented by the facility for the optical alignment system calibration task.

FIG. 16 is a display diagram showing a sample fifth display presented by the facility for the optical alignment system calibration task. FIG. 16 includes page number indicator 1639 and instructions 1624 for moving the T-Frame fixture. FIG. 16 includes a begin test control 1642 that the user may point to in order to begin the test, a test duration indication 1657, and an end test control 1658 that the user may point to in order to end the test. FIG. 16 further includes a test result indication 1644.

Figure 17:
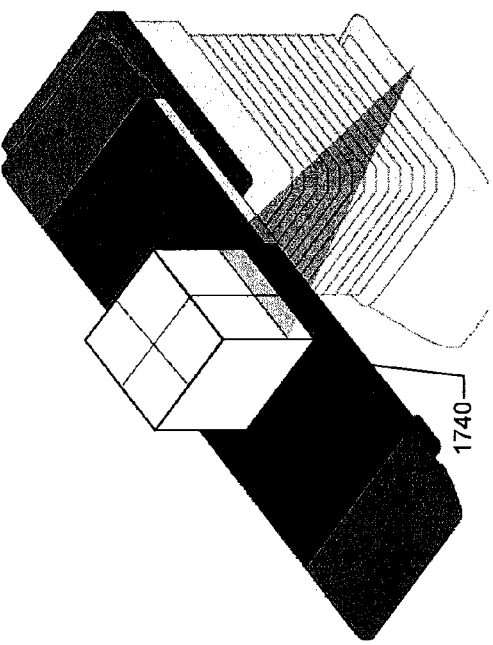
FIG. 17 is a display diagram showing a sample sixth display presented by the facility the for the optical alignment system calibration task.

FIG. 17 is a display diagram showing a sample sixth display presented by the facility for the optical alignment system calibration task. FIG. 17 includes a page number indication 1739, instructions 1724 for placing a cubic calibration fixture on the patient table, and a diagram 1740 showing proper placement of the cubic calibration fixture.

Figure 18:
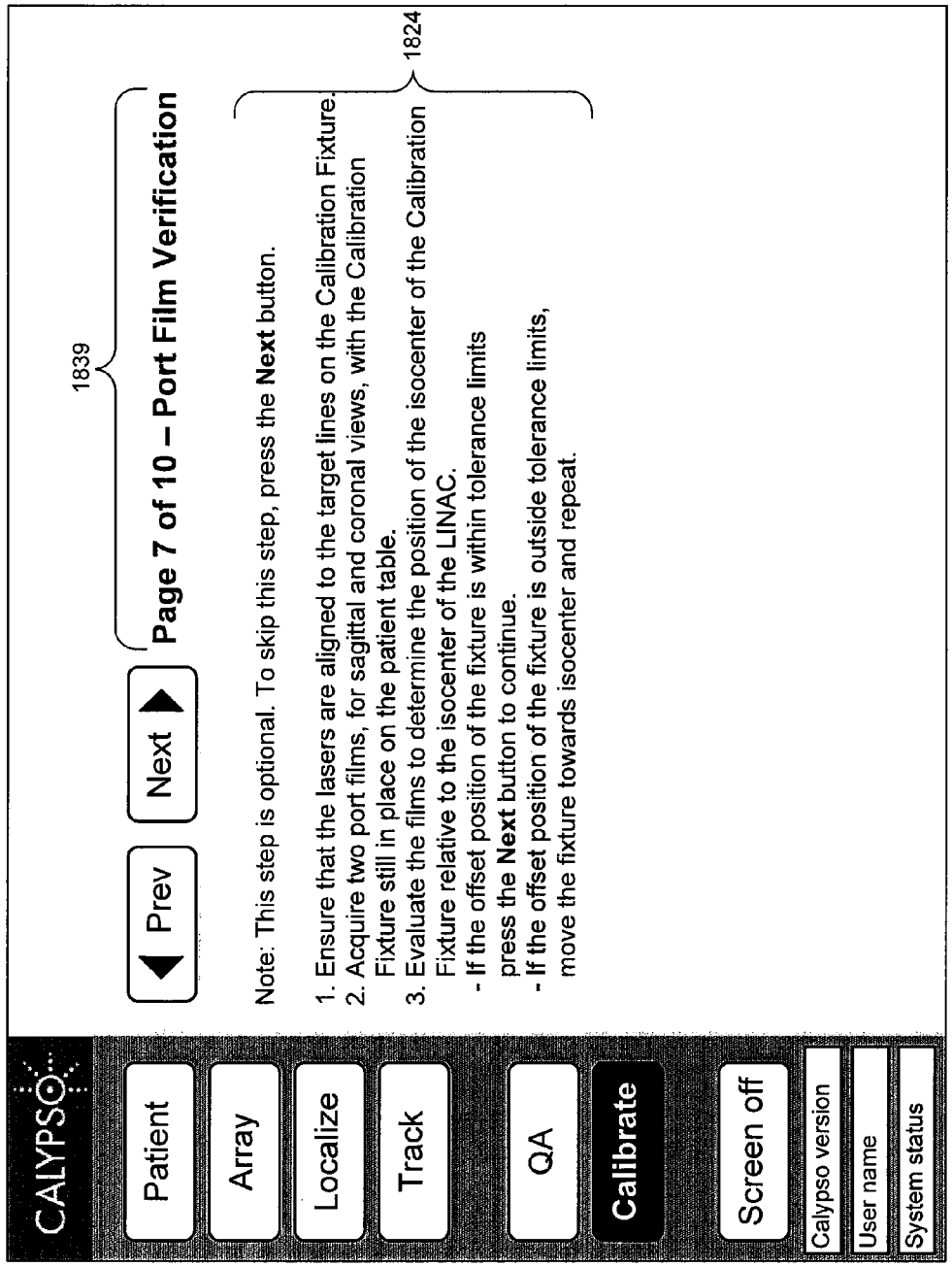
FIG. 18 is a display diagram showing a sample seventh display presented by the facility the optical alignment system calibration task.

FIG. 18 is a display diagram showing a sample seventh display presented by the facility for the optical alignment system calibration task. FIG. 18 includes a page number indication 1839 and instructions 1824.

Figure 19:
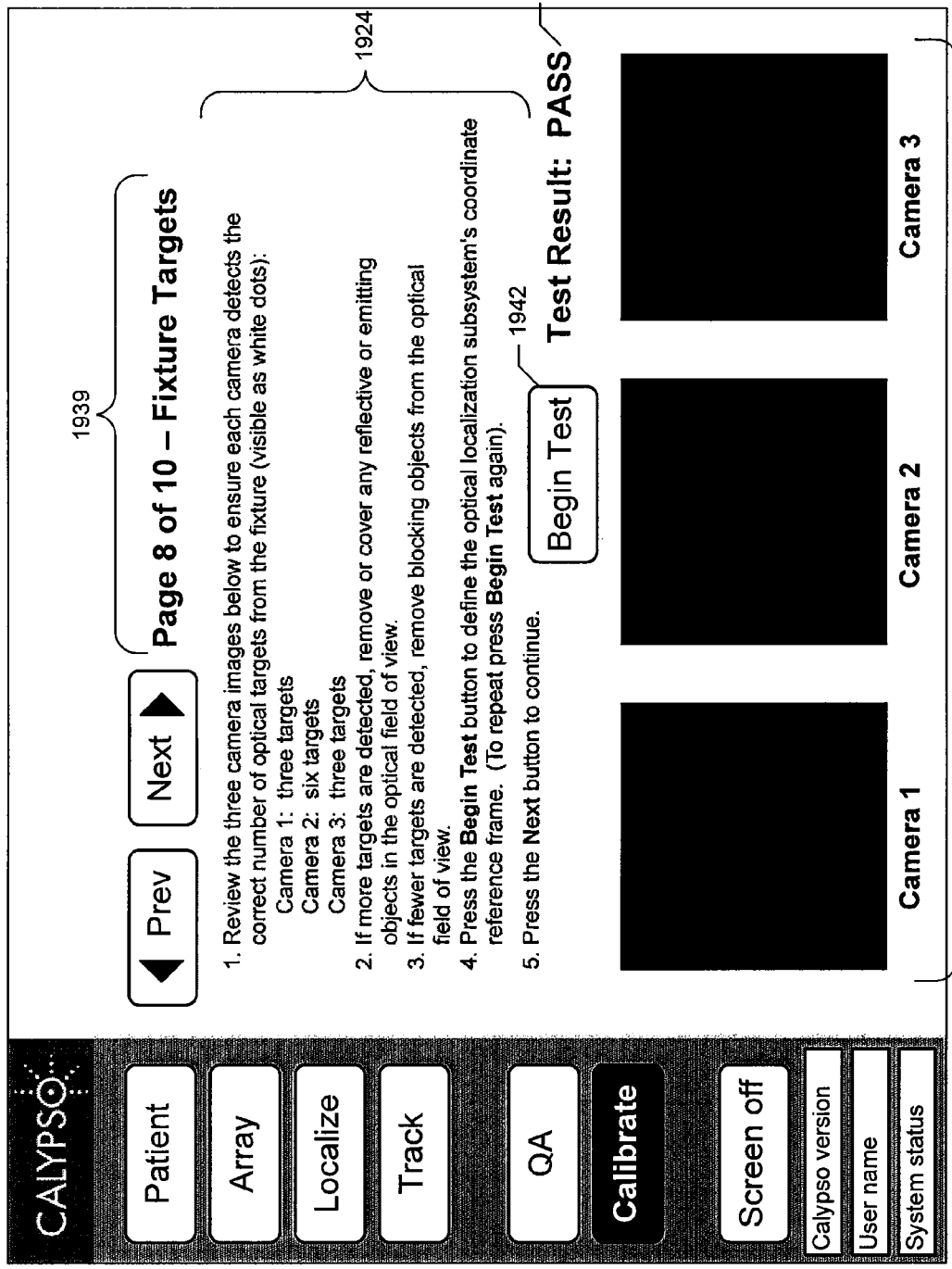
FIG. 19 is a display diagram showing a sample eighth display presented by the facility for the optical alignment system calibration task.

FIG. 19 is a display diagram showing a sample eighth display presented by the facility for the optical alignment system calibration task. FIG. 19 includes a page number indication 1939 and instructions 1924 regarding reviewing the images in camera windows 1951. FIG. 19 further includes a begin test control 1942 that the user may point to in order to begin the test, and a test result indicator 1944.

Figure 20:
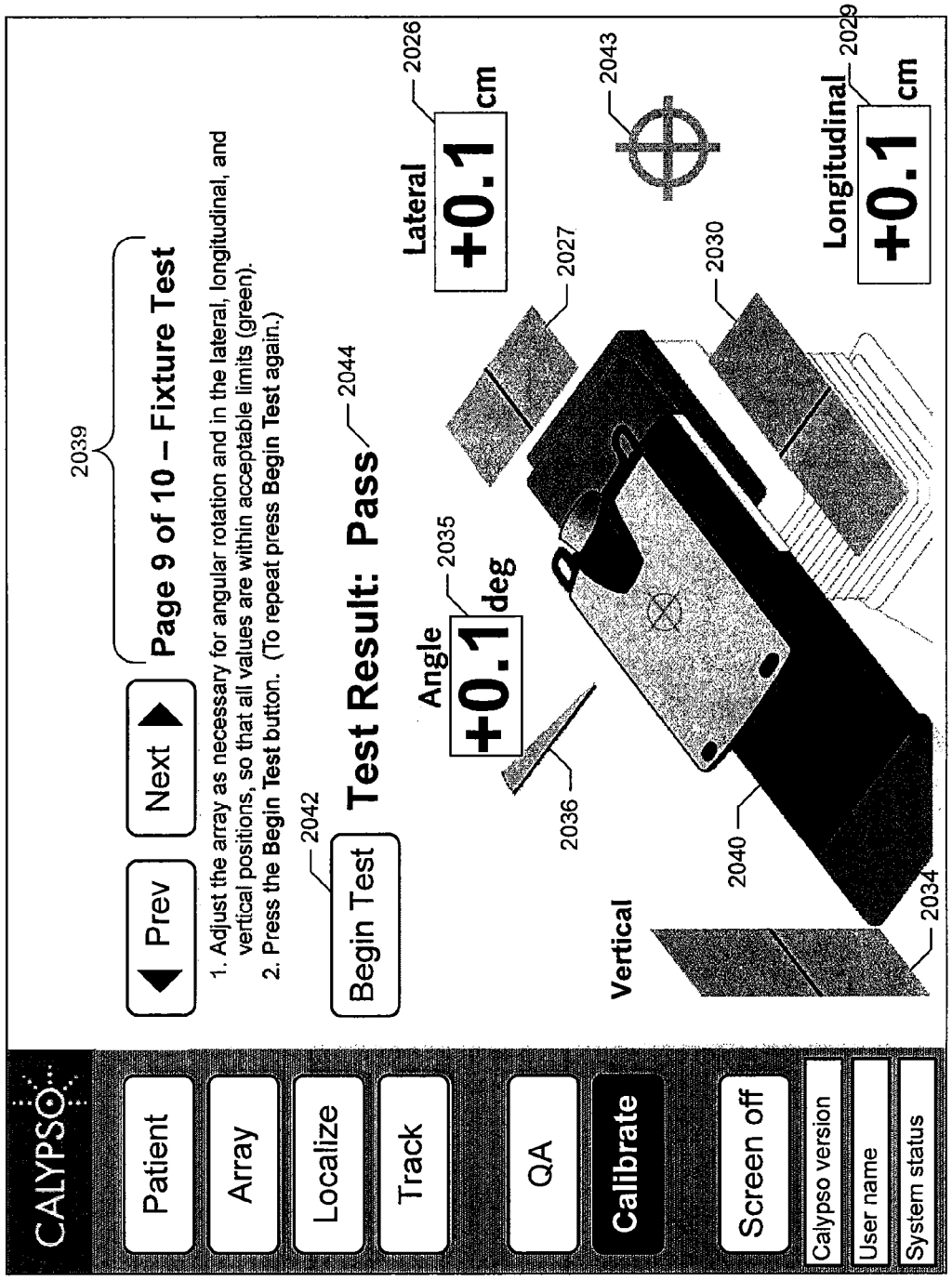
FIG. 20 is a display diagram showing a sample ninth display presented by the facility for the optical alignment system calibration task.

FIG. 20 is a display diagram showing a sample ninth display presented by the facility for the optical alignment system calibration task. FIG. 20 includes a page number indicator 2039 and instructions 2024. FIG. 20 further includes numerical indicators and graphical indicator bars for the lateral, longitudinal, vertical and angle dimensions, and a positioning success indicator 2043. FIG. 20 further includes a begin task control 2042 that the user may point to in order to begin the test, and a test results indictor 2044.

Figure 21:
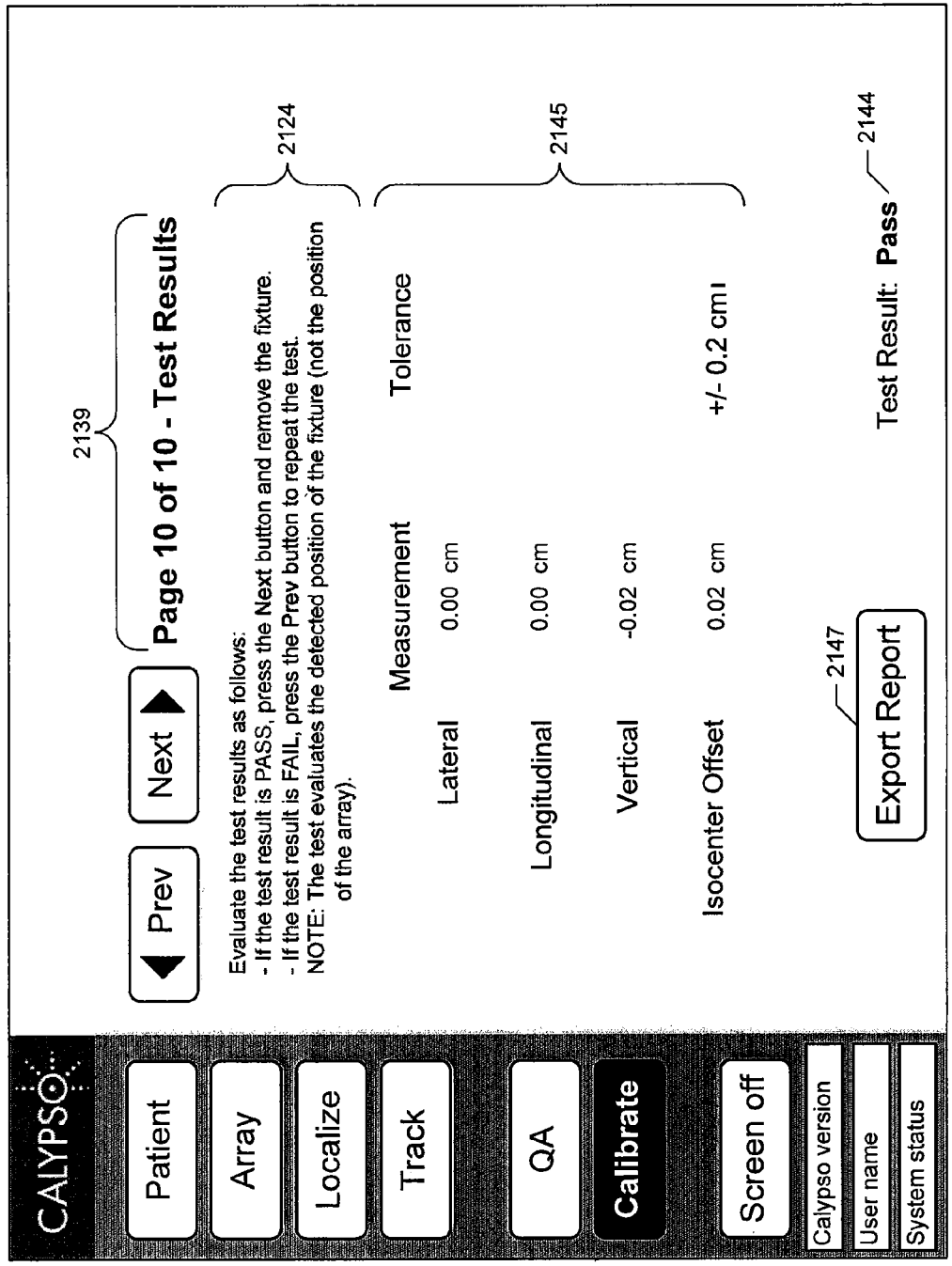
FIG. 21 is a display diagram showing a sample tenth display presented by the facility for the optical alignment system calibration task.

FIG. 21 is a display diagram showing a sample tenth display presented by the facility for the optical alignment system calibration task. FIG. 21 includes a page indicator 2139 and instructions 2124 for acting on the results of the test. Both detailed results 2145 and summary results 2144 are included, as is an export control 2147 that the user may point to in order to export the test results to an external data store.

Figure 22:
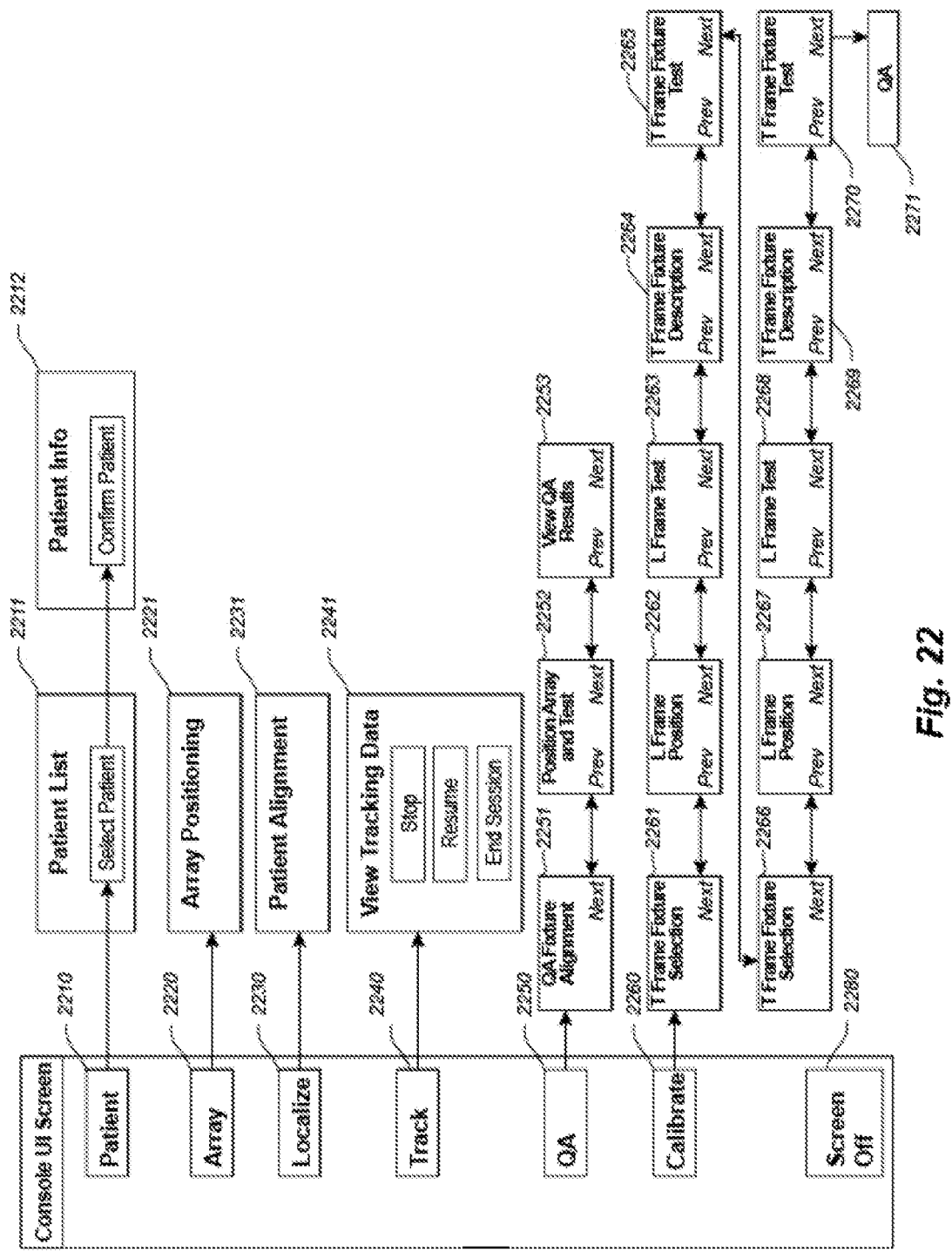
FIG. 22 is a state diagram showing the transition between states, or "screens" shown in FIGS. 3-21 for each task.

FIG. 22 is a state diagram showing the transition between states, or "screens" shown in FIGS. 3-21 for each task. In the patient task 2210, the user interface begins at a patient list screen 2211, shown in FIG. 3. The user transitions to a patient information screen 2212, shown in FIG. 4.

In the array task 2220, the user interface begins in an array positioning screen 2221, shown in FIG. 5.

In the localize task 2230, the user interface begins in the patient alignment screen 2231, shown in FIGS. 6 and 7.

In the track task 2240, the user interface begins at the view tracking data screen 2241, shown in FIG. 8.

In the patient tracking system quality assurance task 2250, the user interface begins at a QA fixture alignment screen 2251, shown in FIG. 9. From there, the user interface transitions to a position array and test screen 2252, shown in FIG. 10. From there, the user interface transitions to a view QA results screen 2253, shown in FIG. 11.

In the optical alignment system calibration task 2260, the user interface begins at a T-Frame fixture selection screen 2261, shown in FIG. 12. From there, the user interface transitions to an L-Frame position screen 2262, shown in FIG. 13. From there, the user interface progresses to an L-Frame test screen 2263, shown in FIG. 14. From there, the facility transitions to a T-Frame fixture description screen 2264, shown in FIG. 15. From there, the user interface transitions to the T-Frame fixture test screen 2265, shown in FIG. 16. From there, the user interface transitions to the calibration fixture alignment screen 2266, shown in FIG. 17. From there, the user interface transitions to the port film verification screen 2267, shown in FIG. 18. From there, the user interface transitions to the calibration fixture targets screen 2268, shown in FIG. 19. From there, the user interface transitions to the calibration fixture test screen 2269, shown in FIG. 20. From there, the user interface transitions to the view calibration test results screen 2270, shown in FIG. 21. In some embodiments, from the view calibration test results screen, the user interface can transition to a QA screen 2271. FIG. 22 further shows a screen off task 2280.

FIGS. 23-28 show a patient wizard that enables a user to create or edit patient information relating to the patient tracking system. FIGS. 23-26 show the four screens of the patient wizard in a new mode, in which data for a new patient is being entered. FIG. 23 is a display diagram showing a sample first display presented by the facility for the patient wizard. The display 2300 includes instructions 2301, fields 2302-2304 into which the user can enter the new patient's name, and field 2305 into which the user can enter an identifier for the patient, such as the patient's social security number. The display 2300 further includes a next control 2392 that the user may select in order to proceed to the next display, and a cancel control 2393 that the user may select in order to cancel the patient wizard.

FIG. 24 is a display diagram showing a sample second display presented by the facility for the patient wizard. The second display enables the user to define a localization plan for the patient, and identify associated personnel. The display 2400 includes instructions 2401; controls 2402 for selecting a usage mode, such as localization alone versus localization and tracking; a control 2403 for selecting transponder implantation date; controls 2404 for selecting tracking limits in each of three dimensions; and controls 2405-2407 for identifying the physician, dosimetrist, and physicist, respectively, for the patient. The display further includes a control 2491 for moving back to the previous display, a control 2492 for moving forward to the next display, and a control 2493 for canceling the patient wizard.

Figure 25:
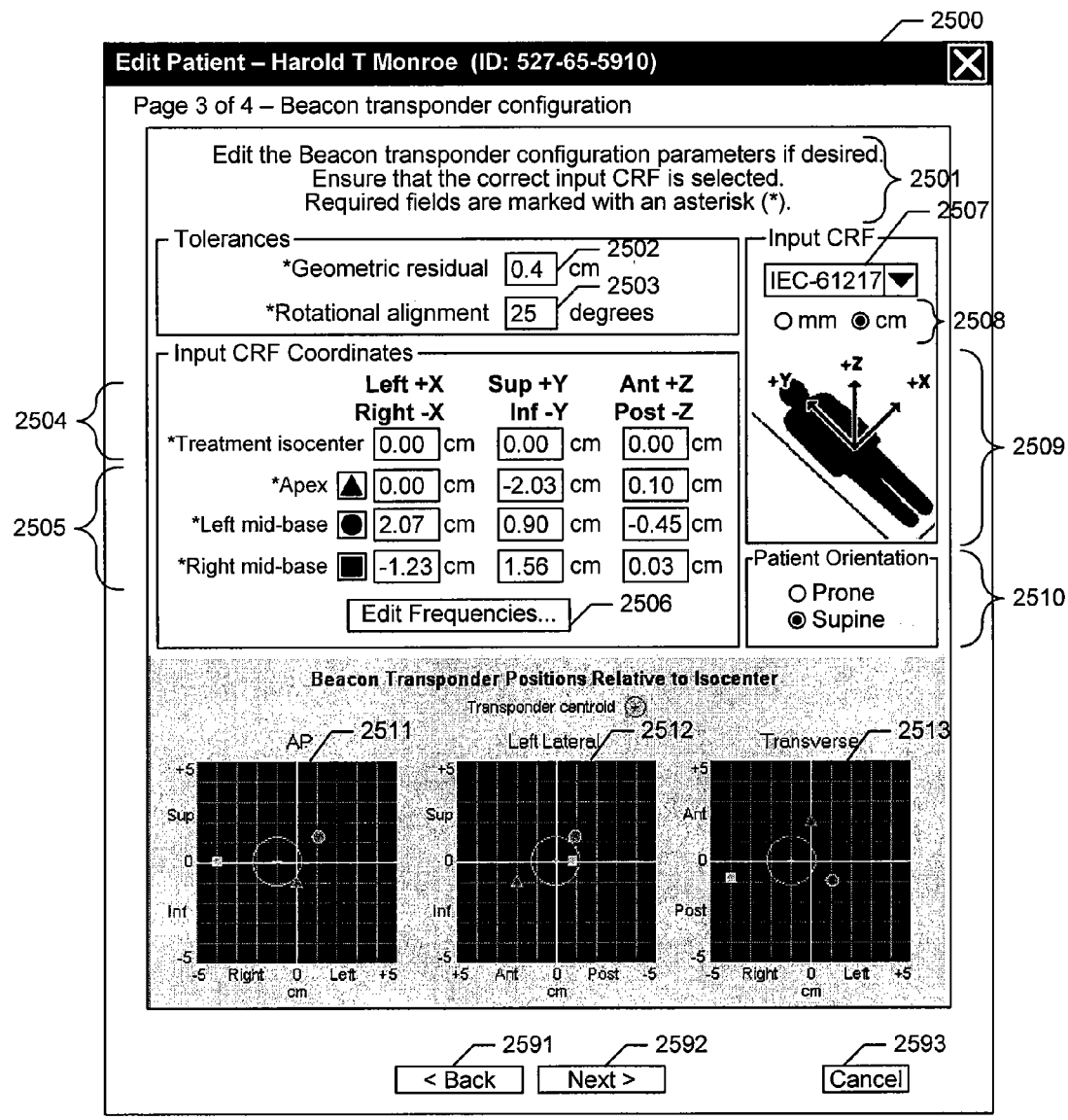
FIG. 25 is a display diagram showing a sample third display presented by the facility for the patient wizard.

FIG. 25 is a display diagram showing a sample third display presented by the facility for the patient wizard. This display enables a user to enter the locations of each of three transponders, edit tracking limits, specify input CRF and patient orientation, view views in three dimensions of the transponder locations, and edit the relationship between a transponder's frequency and position. The display 2500 includes instructions 2501, controls 2502 and 2503 for inputting geometric residual and rotation alignment tolerances; controls 2504 for inputting absolute coordinates for the treatment isocenter; controls 2505 for inputting absolute coordinates of the three transponders; a control 2506 for editing the frequencies of each transponder; a control 2507 for specifying one of the supported coordinate reference frames; controls 2508 for specifying one of the supported units for the selected coordinate reference frame; a diagram 2509 indicating the selected coordinate reference frame relative to a diagram of the patient and the patient table; controls 2510 for selecting patient orientation; and views 2511-2513 showing the locations of the transponders relative to the treatment isocenter from the AP, left lateral, and transverse perspectives. The display further includes a control 2591 for moving back one screen, a control 2592 for moving forward one screen, and a control 2593 for canceling the patient wizard.

FIG. 26 is a display diagram showing a sample fourth display presented by the facility for the patient wizard. This display enables the user to review all entered or edited information for the wizard session. The display 2600 includes instructions 2601; indications 2602-2603 of the information inputted into the first display of the wizard; indications 2604-2609 of the information inputted into the second display of the wizard; and indications 2610-2615 of the information entered or edited in the third display of the wizard. The display further includes a control 2691 for moving back one display, a control 2693 for canceling the patient wizard, and a control 2694 for applying any changes made using the patient wizard.

In some embodiments, the patient wizard may also be used in an edit mode, in which some of the displays differ in some respects from those in the new mode. FIG. 27 is a display diagram showing a sample first display presented by the facility for the patient wizard in the edit mode. It can be seen by comparing FIG. 27 to FIG. 23 that, in the edit mode, the user can edit previously-entered information for the patient other than the patient ID.

Figure 28:
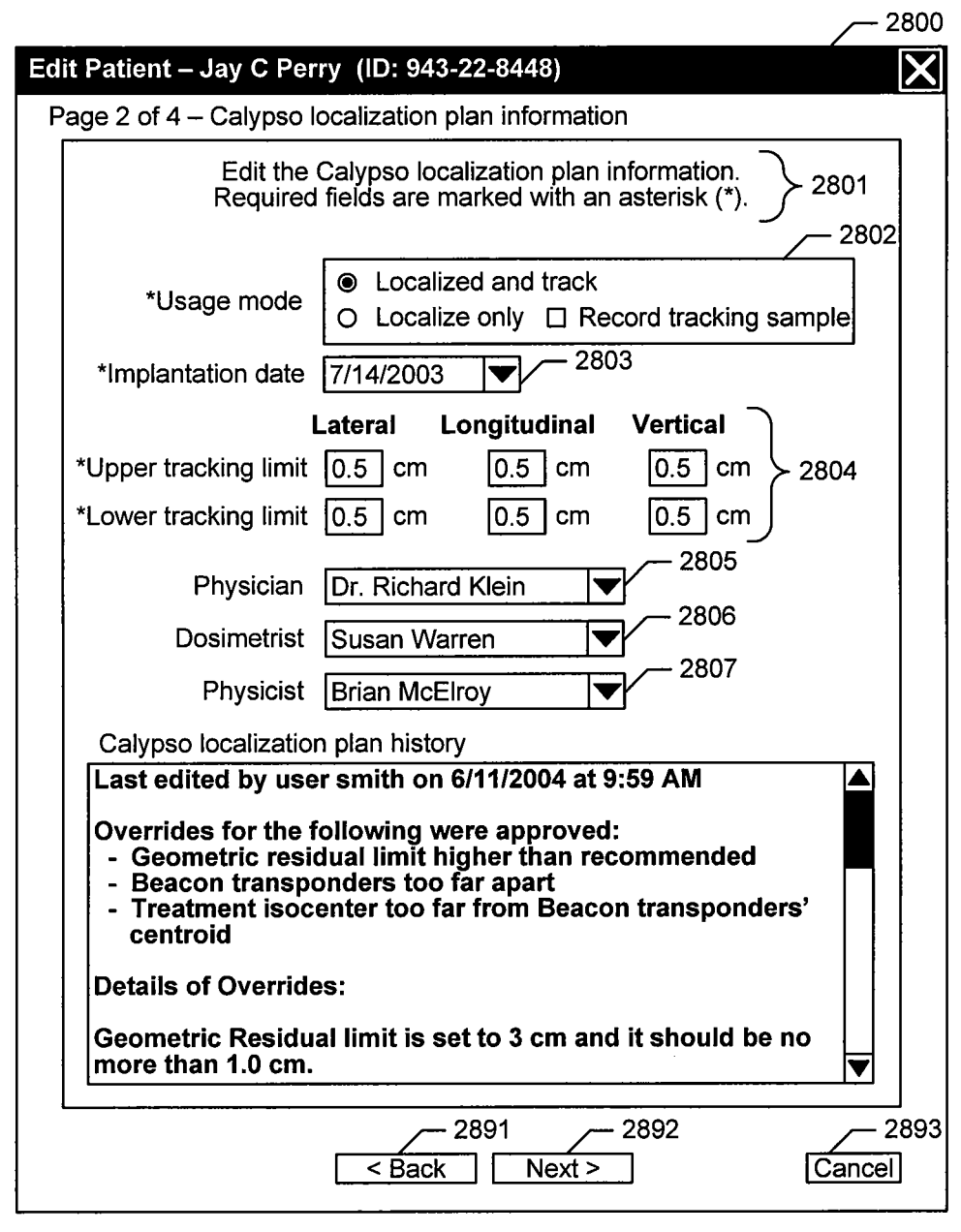

FIG. 28 is a display diagram showing a sample second display presented by the facility for the patient wizard in the edit mode. It can be seen by comparing FIG. 28 to FIG. 24 that, in the edit mode, the user can edit previously-entered information, and view a localization plan history in window 2808.

In some embodiments, in the edit mode, the facility uses third and fourth displays of the patient wizard that are similar to those shown in FIGS. 25 and 26 for the new mode.

In some embodiments the facility restricts the availability of various user interface aspects to users in different classes, or "roles." Table 1 below shows which console user interface tasks are available for Radiation Therapists (RT), Medical Physicists (MP), and Service users:

TABLE 1

| Tasks | RT | MP | Service |
|---|---|---|---|
| Console UI | | | |
| Select a patient | X | X | X |
| Patient session (array positioning, localization, tracking) | X | X | X |
| QA Session | X | X | X |
| OLS Calibration | | X | X |

Table 2 below shows which tracking station tasks are available for Radiation Therapists (RT), Dosimetrists (CMD), Medical Physicists (MP), Administrators (ADM), Medical Physicists (MP), and Service users:

TABLE 2

| Tasks | RT | CMD | MP | ADM | Service |
|---|---|---|---|---|---|
| Tracking Station | | | | | |
| Select a patient | X | | X | | X |
| Manage patients - Create, edit, and delete patients | | X | | | X |
| Generate reports | X | X | X | X | X |
| Export data | X | X | X | X | X |
| Change settings | | X | X | X | X |
| Manage users - Create, edit, delete users and access | | | | X | X |
| Manage T-Frames - Create, edit, delete T-Frames | | | X | X | X |

Additional aspects of the UI presented by some embodiments of the facility are described in U.S. Patent Application No. 60/590,693 filed Jul. 23, 2004, entitled DATA PROCESSING FOR REAL-TIME TRACKING OF A TARGET IN RADIATION THERAPY, and U.S. patent application Ser. No. 11/190205 entitled DATA PROCESSING FOR REAL-TIME TRACKING OF A TARGET IN RADIATION THERAPY, filed concurrently herewith, each of which is hereby incorporated by reference in its entirety.

It will be appreciated by those skilled in the art that the above-described facility may be straightforwardly adapted or extended in various ways. For example, the facility may present a user interface relating to a wide variety of tasks performed in a radiation therapy facility, or in conjunction with locating or tracking implanted passive magnetic transponders. The facility may use a variety of display layouts, formats, styles, colors, fonts, diagrams, and other visual elements, including those not otherwise explicitly shown or discussed herein. The facility may be implemented on a variety of different device types, and used in conjunction with a variety of different kinds of radiation delivery systems, patient tracking systems, treatment enclosures, and other radiation therapy facility equipment. The facility may be used for certain tasks performed separately from radiation therapy, such as tumor localization and/or tracking outside of a radiation treatment facility. While the foregoing description makes reference to various embodiments, the scope of the invention is defined solely by the claims that follow and the elements recited therein.

We claim:

1. A method in a computing system for guiding performance of a process relating to a patient localization and tracking system, comprising:
displaying a user interface in a first state corresponding to a first process task in an ordered sequence of process tasks;
performing the first process task, wherein performing the first process task includes confirming a position of a localization sensor relative to a treatment location;
each time one of the process tasks to which a displayed state of the user interface corresponds is completed, automatically redisplaying the user interface in a state corresponding to a process task following a completed one of the process tasks to which the displayed state of the user interface corresponds;
performing a second process task in the ordered sequence of process tasks after automatically redisplaying the user interface, wherein performing the second process task includes confirming locations of magnetic transponders implanted in a patient; and
performing a third process task in the ordered sequence of process tasks after automatically redisplaying the user interface and confirming that the first and second process tasks have been completed, wherein performing the third process task includes tracking real-time locations of the magnetic transponders via the localization sensor and relative to the treatment location during delivery of radiation therapy.

2. The method of claim 1, further comprising performing a fourth process task in the ordered sequence of process tasks, wherein performing the fourth process task includes performing a quality assurance process.

3. The method of claim 1 wherein a visual user interface is presented for guiding performance of a patient information input process.

4. The method of claim 1 wherein a visual user interface is presented for guiding performance of a patient information editing process.

5. The method of claim 1 wherein the user interface includes a table of contents listing the ordered sequence of process tasks, and wherein, each time the user interface is displayed in a state corresponding to a current process task, the current process task is visually distinguished from other process tasks in the table of contents.

6. The method of claim 1, further comprising:
determining a current role of a user of the visual user interface; and
performing the displaying and redisplaying only if a current user role is among one or more approved roles for the ordered sequence of process tasks.

7. The method of claim 1, further comprising receiving a stream of positioning data relating to a radiation therapy session task.

8. A computing system for guiding performance of a radiation therapy session, comprising:
a display that displays a user interface in a first state corresponding to a first radiation therapy session task in an ordered sequence of radiation therapy session tasks;
a display updater that, each time the radiation therapy session task to which a displayed state of the user interface corresponds is completed, redisplays the user interface in a state corresponding to a radiation therapy session task following the radiation therapy session task to which the displayed state of the user interface corresponds; and
a patient localization and tracking system configured to perform the first radiation therapy session task, perform a second radiation therapy session task in the ordered sequence of process tasks after automatically redisplaying the user interface, and perform a third radiation therapy session task in the ordered sequence of process tasks after redisplaying the user interface and completing the first and second radiation therapy tasks, wherein the first radiation therapy task includes confirming a position of a localization sensor relative to a treatment location, wherein the second radiation therapy task includes confirming locations of magnetic transponders implanted in a patient, and the third radiation therapy task includes tracking real-time locations of the magnetic transponders via the localization sensor and relative to the treatment location during delivery of radiation therapy.

9. The computing system of claim 8, further comprising a receiver that receives a stream of positioning data relating to a radiation therapy session task.

10. The computing system of claim 9 wherein the positioning data indicates a vertical position, a lateral position, and a longitudinal position of the patient relative to the treatment location, and wherein indications of the vertical position, lateral position, and longitudinal position are separately displayed at the display in conjunction with a pictorial representation of the patient and the localization sensor array.

11. The computing system of claim 9 wherein the positioning data indicates at least one of location and orientation of the patient relative to the treatment location.

12. The computing system of claim 9 wherein the positioning data includes at least one of a location measure and an orientation measure, and wherein each measure has a predetermined tolerance about a target value, and wherein each value is displayed at the display in a first color when the target value is outside its predetermined tolerance and in a second color when within its predetermined tolerance.

13. A computer-readable non-transitory storage medium whose contents cause a computing system to perform a method for guiding performance of a process relating to a patient localization and tracking system, comprising:
displaying a user interface in a first state corresponding to a first process task in an ordered sequence of process tasks;
each time one of the process tasks to which a displayed state of the user interface corresponds is completed, automatically redisplaying the user interface in a state corresponding to a process task following a completed one of the process tasks to which the displayed state of the user interface corresponds, wherein the re-displaying includes displaying the user interface in a second state corresponding to a second process task, and displaying the user interface in a third state corresponding to a third second process task; and
performing the first process task, the second process task, and the third process task, wherein the performing includes performing the third process task, after the first and second process tasks are completed,
wherein performing the first process task includes confirming a position of a localization sensor relative to a treatment location, performing the second process task includes confirming locations of magnetic transponders implanted in a patient, and the third process task includes tracking real-time locations of the magnetic transponders via the localization sensor and relative to the treatment location during delivery of radiation therapy.

14. The computer-readable non-transitory medium of claim 13 wherein performing the third process task in the method further includes receiving a stream of data that includes positioning data relating to a task in a radiation therapy session.

15. The computer-readable non-transitory medium of claim 14 wherein the positioning data indicates at least one of location and orientation of the localization sensor array relative to the treatment location.

16. The computer-readable non-transitory medium of claim 14 wherein the method further includes includes displaying at least one of a location measure and an orientation measure included in the positioning data, and wherein each displayed measure has a predetermined tolerance about a target value, and wherein each value is displayed in a first color when outside its predetermined tolerance and in a second color when within its predetermined tolerance.

17. The computer-readable non-transitory medium of claim 14 wherein the positioning data indicates a lateral position, a longitudinal position, and an angular orientation of the localization sensor array relative to the treatment location, and wherein the lateral position, longitudinal position, and angular orientation are separately displayed in conjunction with a pictorial representation of the patient and the localization sensor array.

18. The method of claim 17 wherein the lateral position, longitudinal position, and angular orientation are displayed in numerical form.

19. The method of claim 17 wherein the lateral position, longitudinal position, and angular orientation are displayed in graphical form.

20. The method of claim 17 wherein the lateral position, the longitudinal position, and the angular orientation are each displayed in a color indicative of whether the lateral position, the longitudinal position, or the angular orientation is within a preselected tolerance.

21. The computer-readable non-transitory medium of claim 14 wherein displaying the positioning data of the mehtincludes displaying a bar graph of each of at least one of a location measure and an orientation measure included in the positioning data, and wherein each measure for which a bar graph is displayed has a predetermined tolerance about a target value, and wherein each bar graph is displayed in a first color when its measure is outside its predetermined tolerance and in a second color when its measure is within its predetermined tolerance.

22. The computer-readable non-transitory medium of claim 14 wherein the method further includes displaying a time-series graph of each of at least one of a location measure and an orientation measure included in the positioning data, and wherein each measure for which a time-series graph is displayed has a predetermined tolerance about a target value, and wherein each time-series graph is displayed in a first color when its measure is outside its predetermined tolerance and in a second color when its measure is within its predetermined tolerance.

* * * * *